United States Patent [19]

Iwao et al.

[11] Patent Number: 4,552,969

[45] Date of Patent: Nov. 12, 1985

[54] 3-ALKANOYL BENZOTHIAZOLINE COMPOUNDS USEFUL FOR TREATING CARDIOVASCULAR DISEASE

[75] Inventors: Jun-ichi Iwao, Takarazuka; Tadashi Iso, Sakai; Masayuki Oya, Ibaraki, all of Japan

[73] Assignee: Santen Pharmaceutical Co., Ltd., Osaka, Japan

[21] Appl. No.: 612,322

[22] Filed: May 21, 1984

Related U.S. Application Data

[62] Division of Ser. No. 503,160, Apr. 14, 1983, Pat. No. 4,479,949.

[30] Foreign Application Priority Data

Sep. 12, 1981 [JP] Japan ............................ 56-144148

[51] Int. Cl.$^4$ .................... C07D 91/16; C07D 417/00
[52] U.S. Cl. .................................. 548/179; 544/135; 546/198; 546/200; 546/209; 546/270
[58] Field of Search ........................ 548/179; 424/270; 546/200, 209, 280, 198, 270; 514/321, 338, 367

[56] References Cited

U.S. PATENT DOCUMENTS

| | | | |
|---|---|---|---|
| 2,996,512 | 8/1961 | Stephens | 548/179 |
| 3,117,124 | 1/1964 | Krapcho | 548/179 |
| 3,574,218 | 4/1971 | Hideg et al. | 548/179 |
| 3,720,683 | 3/1973 | Breuer et al. | 548/179 |

OTHER PUBLICATIONS

Merck Index, 10th Edition, 6446, 6453, 2254, 2676, 8928.
Cossey et al., J. Chem. Soc. 1965, p. 954.
Palmer et al., J. Med. Chem. 14, p. 248.
Breuer et al., Chem. Abst. vol. 79 (1973) 18693u.
De Simone et al., Chem. Abst. vol. 90 (1979) 54891t.
De Simone et al., Chem. Abst. vol. 93 (1980) 132429b.
Santen Pharmaceutical Co. Ltd. Chem. Abst. 22453w.

Binger, Medicinal Chem., 2nd edition, pp. 42–43.

Primary Examiner—Donald G. Daus
Assistant Examiner—Cecilia Shen
Attorney, Agent, or Firm—Frishauf, Holtz, Goodman & Woodward

[57] ABSTRACT

The invention relates to benzothiazoline derivatives of the formula [I] and salts thereof, which are useful for (i) treating cardiovascular diseases, and (ii) as the active ingredient of pharmaceutical compositions. Formula [I] follows:

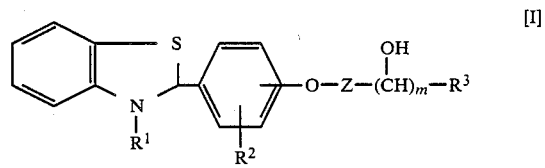

wherein
$R^1$ is lower alkanoyl;
$R^2$ is one or more group(s) selected from hydrogen, lower alkyl, lower alkoxy, hydroxy, halogen, nitro, halogenolower alkyl and sulfamoyl;
$R^3$ is

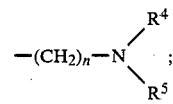

$R^4$ and $R^5$ each is hydrogen, lower alkyl, cyclohexyl or substituted lower alkyl;
Z is straight or branched alkylene containing 1 to 6 carbon atoms;
m is 0 or 1; n is 0 or 1; and p is 4 or 5.

24 Claims, No Drawings

3-ALKANOYL BENZOTHIAZOLINE COMPOUNDS USEFUL FOR TREATING CARDIOVASCULAR DISEASE

TECHNICAL FIELD OF THE INVENTION

This is a division of application Ser. No. 503,160 filed Apr. 14, 1983 now U.S. Pat. No. 4,479,949, issued Oct. 30, 1984.

This invention relates to benzothiazoline derivatives of the formula [I] and salts thereof,

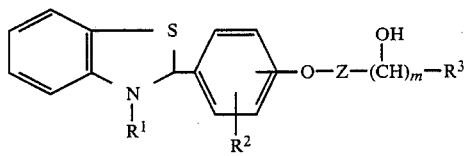

wherein
$R^1$ is lower alkanoyl;
$R^2$ is one or more group(s) selected from hydrogen, lower alkyl, lower alkoxy, hydroxy, halogen, nitro, halogeno-lower alkyl and sulfamoyl;
$R^3$ is

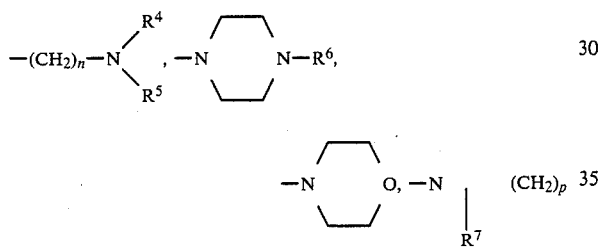

or —$COR^8$;
$R^4$ and $R^5$, which may be same or different, each is hydrogen, lower alkyl, cyclohexyl or substituted lower alkyl wherein the substituent(s) is/are selected from the group consisting of hydroxy, phenyl, pyridyl, piperidyl or phenylcarbonyl, and said phenyl nucleus may be resubstituted by one or more groups selected from lower alkyl, hydroxy, halogen, lower alkoxy, nitro, cyano, acetamino and lower alkylamino;
$R^6$ is hydrogen, alkyl containing 1 to 8 carbon atoms, alkanoyl containing 2 to 8 carbon atoms, alkenoyl containing 2 to 8 carbon atoms or furylcarbonyl, each of which alkyl, alkanoyl and alkenoyl may be substituted by one or more groups selected from hydroxy, phenyl and phenylcarbonyloxy, and said phenyl nucleus may be resubstituted by one or more groups selected from lower alkyl, hydroxy, halogen, lower alkoxy, nitro, cyano, acetamino and lower-alkylamino;
$R^7$ is hydrogen, hydroxy, phenyl-lower alkyl or benzoyl;
$R^8$ is hydroxy, lower alkoxy,

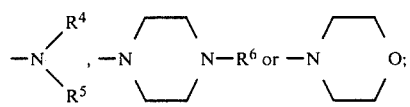

Z is straight or branched alkylene containing 1 to 6 carbon atoms;
m is 0 or 1;
n is 0 or 1;
p is 4 or 5,
wherein the terms lower alkyl, lower alkoxy and lower alkanoyl refer to groups having 1 to 6 carbon atoms.
The same shall be applied hereinafter.

BACKGROUND OF THE INVENTION

The compounds of this invention are novel benzothiazoline derivatives wherein the substituent at 3-position on the benzothiazoline ring is lower alkanoyl and that at 2-position is phenyl which is resubstituted by ether group at any position. 2-Phenylbenzothiazoline derivatives were reported by H. Breuer et al. (U.S. Pat. No. 3,720,683), H. D. Cossey et al. (J. Chem. Soc., 1965, 954) and P. J. Palmer et al. (J. Med. Chem., 14, 248). The U.S. Pat. of Breuer et al. relates to 2-phenylbenzothiazoline derivatives in which phenyl nucleus is substituted by alkyl, etc. but not ether group, and the pharmacological effects are for anti-inflammatory and anti-microbiral. Cossey et al. and Palmer et al. reported 2-phenylbenzothiazoline derivatives in which phenyl nucleus is substituted by ether group, but the substituent of 3-position is not lower alkanoyl but hydrogen, alkyl, benzyl, etc., and the pharmacological effect is for anti-microbial.

DETAILED DESCRIPTION OF THE INVENTION

This invention relates to benzothiazoline derivatives of the formula [I].

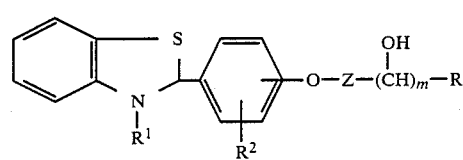

The compounds of this invention are benzothiazoline derivatives wherein the substituent at 3-position on the benzothiazoline ring is lower alkanoyl and that at 2-position is phenyl which is resubstituted by ether group at any position. The compounds of this invention are not only new in chemical structure but also found useful for treatment of cardiovascular diseases and such effect on cardiovascular diseases has not been found in the known benzothiazoline derivatives. Cardiovascular diseases are angina cordis, arrhythmia, thrombosis, etc., and β-blocker, inhibitor of platelet aggregation, calcium antagonist, etc. are used as therapeutic agent. From the pharmacological tests, it is proved that the compounds of this invention possess a superior platelet anti-aggregation effect and calcium antagonization, so they are useful for cardiovascular diseases. Processes for preparing the compounds of this invention are summarized as follows. The reaction of the compound of the formula [II] with the compound of the formula [III],

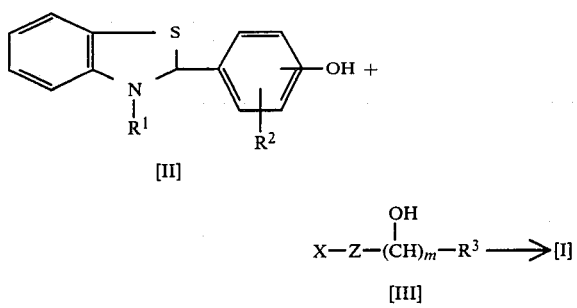

[II]

$$X-Z-(CH)_m-R^3 \longrightarrow [I]$$

[III]

wherein X is halogen (the same shall be applied hereinafter), or the reaction reversed the above reaction order, i.e., the reaction of the compound of the formula [IV] with the amine derivative,

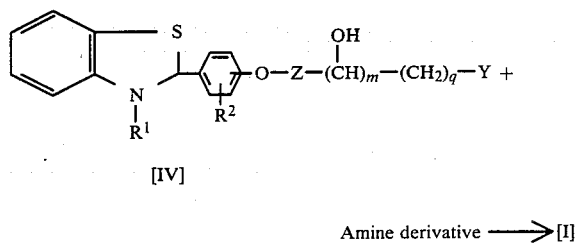

[IV]

Amine derivative ⟶ [I]

wherein
Y is halogen, carboxy or formyl, and Y and —OH may be jointed to form epoxy ring;
Amine derivative is

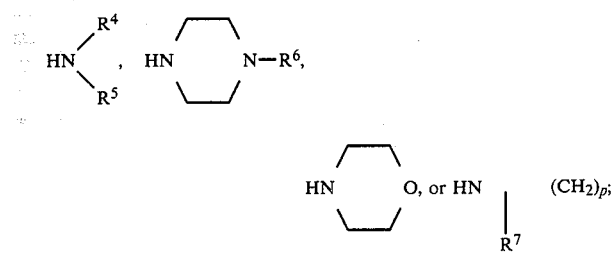

q is 0 or 1,
the same shall be applied hereinafter.

The processes are explained in detail as follows. The reaction of the hydroxy derivative of the formula [II] with the halide of the formula [III] needs no specific conditions, and known methods which are generally used for a reaction or hydroxy derivative with halide can be employed, but preferably the reaction is carried out in organic solvent (for example, dimethylformamide) in the presence of base (for example, NaH). The reaction of the compound of the formula [IV] with amine derivative is divided into the following (a)-(d) reactions.

(a)

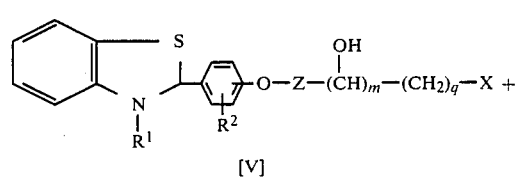

[V]

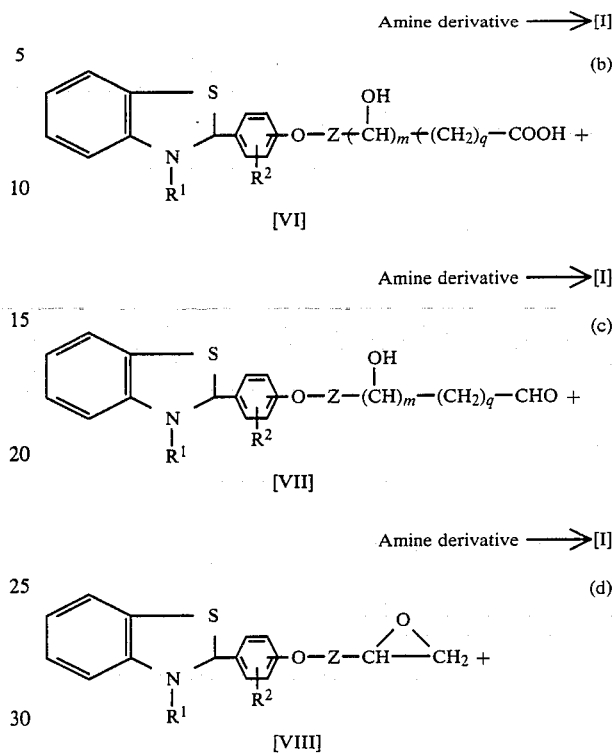

Specific conditions are unnecessary for the above-mentioned reactions. Methods which are generally used for a reaction of amine derivative with halide, carboxylic acid derivative, aldehyde derivative or epoxy derivative can be employed.

The compounds of this invention can be converted to acid salts. Said salts are obtained by general methods using inorganic acids or organic acids. Examples of pharmaceutically acceptable salts of the compounds are hydrochloride salt, sulfuric acid salt, phosphoric acid salt, lactic acid salt, maleic acid salt, fumaric acid salt, methanesulfonic acid salt, p-toluenesulfonic acid salt, oxalic acid salt, etc.

The compounds of the formula [I] have stereoisomers because of the existence of one or more asymmetric carbon atoms, and these isomers are included in this invention.

Examples are shown below, and the compounds of this invention are listed in Table I–IX.

The assignments of the NMR spectra in Table X are made according to the numbers of the formula [IX].

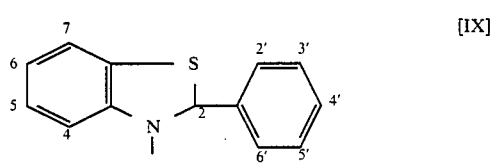

But, protons (aromatic), not be assigned, are named as aromatic H (Ar—H). Proton of —OCH$_3$ group is assigned as —OCH$_3$(P) when the group is attached to $C_2'$-$C_6'$ position of the formula [IX], and assigned as —OCH₃(A) when the group is attached to the phenyl group which is the substituent of amine moeity of the side chain.

EXAMPLE 1

3-Acetyl-2-[2-(3-t-butylamino-2-hydroxypropoxy)-phenyl]benzothiazoline hydrochloride (Compound No. 86)

1.31 g of 3-acetyl-2-[2-(2,3-epoxypropoxy)phenyl]-benzothiazoline and 4.21 ml of t-butylamine are dissolved in 10 ml of ethanol and the solution is refluxed for 1 hour. After cooling, 2 ml of 2N HCl/ethyl acetate is added to the reaction mixture and the solution is concentrated in vacuo. To the residue ether is added to produce crystals. Crystals are collected by filtration to give 1.3 g (81%) of the titled compound.

Physical data are shown in Table VII.

The compounds shown in Table VII are prepared by the similar method descrived above using corresponding amine derivatives.

EXAMPLE 2

3-Acetyl-2-[2-(3-t-butylamino-2-hydroxypropoxy)-phenyl]benzothiazoline hydrochloride (Compound No. 86)

1.64 g of 3-acetyl-2-[2-(2,3-epoxypropoxy)phenyl]-benzothiazoline, 1.82 g of 3-acetyl-2-[2-(3-chloro-2-hydroxypropoxy)phenyl]benzothiazoline and 10 ml of t-butylamine are dissolved in 30 ml of ethanol and the solution is refluxed for 3 hours. The solution is concentrated in vacuo, and the residue is dissolved in ethyl acetate. The solution is washed with saturated sodium chloride solution and dried over anhydrous magnesium sulfate. To this solution 2N HCl/ether is added to produce crystals. Crystals are filtered to give 3.5 g (80%) of the titled compound.

The physical constant of the crystals is the same of the compound obtained in Example 1.

EXAMPLE 3

3-Acetyl-2-[2-(3-dimethylaminopropoxy)phenyl]benzothiazoline (Compound No. 7)

To the suspension of 0.26 g of the sodium hydride in anhydrous DMF, the solution of 1.36 g of 3-acetyl-2-(2-hydroxyphenyl)benzothiazoline in 5 ml of anhydrous DMF is added dropwise under nitrogen atmosphere at room temperature. After the addition, the reaction mixture is stirred for 20 minutes at room temperature. To the reaction mixture, the solution of 0.61 g of 3-dimethylaminopropyl chloride in 10 ml of anhydrous DMF is added. The reaction mixture is stirred for 2 hours at 80° C., and washed with n-hexane after cooling and poured into ice-water. The separated oil is extracted with ethyl acetate. The organic layer is washed with N—NaOH solution, water and saturated sodium chloride solution in the order named and dried over anhydrous magnesium sulfate. Ethy acetate is removed off in vacuo to give 1.0 g (56%) of the titled compound.

Physical data are shown in Table I.

The compounds shown in Table I, II and III are prepared by the similar method described above using corresponding benzothiazoline derivatives and substituted aminoalkyl halides.

EXAMPLE 4

3-Acetyl-2-[2-(3-aminopropoxy)phenyl]benzothiazoline hydrochloride (Compound No. 1)

By substituting 0.83 g of 3-aminopropyl bromide for 3-dimethylaminopropyl chloride in the procedure of Example 3, 1.2 g of the titled compound is obtained.

Physical data are shown in Table I.

EXAMPLE 5

3-Acetyl-2-[2-(3-diethylaminopropoxy)phenyl]benzothiazoline hydrochloride (Compound No. 10)

To the solution of 3.48 g of 3-acetyl-2-[2-(3-chloropropoxy)phenyl]benzothiazoline in 20 ml of ethanol, 10.3 ml of diethylamine is added and the mixture is refluxed for 2 hours. After removal of ethanol and excess amount of diethylamine in vacuo, ethyl acetate and water are added to the residue. The organic layer is extracted with N-hydrochloric acid, the acidic layer is alkalinized with N-sodium hydroxide solution and extracted with ethyl acetate. The organic layer is washed with saturated sodium chloride solution and dried over anhydrous magnesium sulfate. The solvent is removed off in vacuo and the resulting oil is dissolved in methanol. To the solution hydrochloric acid in ethyl acetate is added to give 3.4 g (80%) of the titled compound.

Physical data are shown in Table I.

The compounds shown in Table I, II, III and VIII are prepared by the similar method described above using corresponding benzothiazoline derivatives and amine derivatives.

EXAMPLE 6

3-Acetyl-2-[2-(3-methylaminopropoxy)phenyl]benzothiazoline fumarate (Copmpound No. 2)

To the solution of 6.55 g of 3-acetyl-2-[2-(3-oxopropoxy)phenyl]benzothiazoline in 100 ml of methanol, 8.10 g of methylamine hydrochloride and 10.0 g of molecular sieves(3A), smashed into fine pieces, are added. To the suspension 1.26 g of sodium cyano borohydride is added and the mixture is stirred for 1 hour at room temperature. 2N-Hydrochloric acid is added to the reaction mixture and methanol is removed off in vacuo. The aqueous layer is washed with ethyl acetate and alkalinized with 2N-sodium hydroxide solution and extracted wiht ethyl acetate. The organic layer is washed with saturated sodium chloride solution and dried over anhydrous magnesium sulfate. The solvent is removed off in vacuo and the resulting oil is dissolved in methanol. To the solution fumaric acid and ethyl acetate are added to give 4.9 g (65%) of the titled compound.

Physical data are shown in Table I.

EXAMPLE 7

3-Acetyl-2-[2-[5-(N-cyclohexyl-N-methlamino)pentyloxy]-5-methoxyphenyl]benzothiazoline fumarate (Compound No. 21)

By substituting 4.50 g of 3-acetyl-2-[2-(5-bromopentyloxy)-5-methoxyphenyl]benzothiazoline for 3-acetyl-2-[2-(3-chloropropoxy)phenyl]benzothiazoline and 3.40 g of N-methylcyclohexylamine for diethylamine in the procedure of Example 5, 4.2 g (70%) of the titled compound is obtained.

Physical data are shown in Table I.

The compounds shown in Table I are prepared by the similar method described above using corresponding benzothiazoline derivatives and amine derivatives.

EXAMPLE 8

3-Acetyl-2-[3-[3-(N-cyclohexyl-N-methylamino)-propoxy]-4-hydroxyphenyl]benzothiazoline fumarate (Compound No. 37)

3.64 g of 3-acetyl-2-[3-(3-chloropropoxy)-4-hydroxyphenyl]benzothiazoline and 3.40 g of N-methylcyclohexylamine are stirred at 100° C. for 1 hour. After cooling to room temperature, the reaction mixture is dissolved in 50 ml of chloroform, the solution is washed with N-hydrochloric acid, N-sodium hydroxide solution and saturated sodium chloride solution in the named order and dried over anhydrous magnesium sulfate. Chloroform is removed off in vacuo and the residue is purified by silica gel column chromatography. The oily product is dissolved in 20 ml of ethyl acetate. To the solution 0.71 g of fumaric acid in 3 ml of methanol is added to give 2.78 g (50%) of the titled compound.

Physical data are shown in Table II.

The compounds shown in Table II and III are prepared by the similar method described above using corresponding bnezothiazoline derivatives and amine derivatives.

EXAMPLE 9

3-Acetyl-2-[2-[2-[4-(3,4-dimethoxyphenetyl)-1-piperazinyl]ethoxy]phenyl]benzothiazoline dimaleate (Compound No. 57)

3.34 g of 3-acetyl-2-[2-(2-chloroethoxy)phenyl]benzothiazoline and 5.01 g of 1-(3,4-dimethoxyphenetyl)-piperazine are stirred at 110° C. for 1 hour. After cooling to room temperature, the reaction mixture is dissolved in 50 ml of chloroform, the solution is washed with N-hydrochloric acid, N-sodium hydroxide solution and saturated sodium chloride solution in the named order and dried over anhydrous magnesium sulfate. Chloroform is removed off in vacuo and the resulting oil is dissolved in 50 ml of ethyl acetate. To the solution 2.32 g of maleic acid in 30 ml of ethyl acetate is added to give 6.24 g (80%) of the titled compound.

Physical data are shown in Table IV.

The compounds shown in Table I, IV, V, VI and VIII are prepared by the similar method described above using corresponding benzothiazoline derivatives and amine derivatives.

EXAMPLE 10

3-Acetyl-2-[2-[3-(ethoxycarbonyl)propoxy]phenyl]benzothiazoline (Compound No. 97)

To the suspension of 1.59 g of sodium hydride in 30 ml of anhydrous DMF, the solution of 8.13 g of 3-acetyl-2-(2-hydroxyphenyl)benzothiazoline in 30 ml of anhydrous DMF is added dropwise under nitrogen atmosphere at room temperature. After the addition, the reaction mixture is stirred for 20 minutes at room temperature. To the reaction mixture, the solution of 4.95 g of ethyl 4-chlorobutyrate in 15 ml of anhydrous DMF is added and stirred for 5 hours at 70° C. After cooling to room temperature the reaction mixture is poured into ice-water and extracted with ethyl acetate.

The organic layer is washed with N-potassium hydroxide solution, water, N-hydrochloric acid and saturated sodium chloride solution in the named order and dried over anhydrous magnesium sulfate. The solvent is removed off and the resulting oil is purified by silica gel column chromatography to give 8.67 g (75%) of the titled compound.

Physical data are shown in Table IX.

EXAMPLE 11

3-Acetyl-2-[2-[3-(carboxy)propoxy]phenyl]benzothiazoline (Compound No. 96)

To the solution of 7.71 g of 3-acetyl-2-[2-[3-(ethoxycarbonyl)propoxy]phenyl]benzothiazoline in 50 ml of methanol, 2N-sodium hydroxide solution is added and the reaction mixture is stirred for 2 hours at room temperature. Methanol is removed off in vacuo. The residue is acidified with 2N-hydrochloric acid to give 5.72 g (80%) of the titled compound.

Physical data are shown in Table IX.

EXAMPLE 12

3-Acetyl-2-[2-[3-(morpholinocarbonyl)propoxy]-phenyl]benzothiazoline (Compound No. 100)

To the solution of 1.79 g of 3-acetyl-2-[2-[3-(carboxy)propoxy]phenyl]benzothiazoline and 0.51 g of triethylamine in 20 ml of anhydrous methylene chloride, 0.68 g of isobutyl chloroformate is added dropwise while stirring at −13° C. and stirred additional 10 minutes at the same temperature. To the solution 0.44 g of morpholine in 5 ml of methylene chloride is added dropwise.

After the addition, the reaction mixture is stirred for 1 hour under ice-water cooling and for 1 hour at room temperature. The reaction mixture is washed with 5% citric acid solution, water, N-potassium hydroxide solution and saturated sodium chloride solution in the named oder and dried over anhydrous magnesium sulfate. The solvent is removed off in vacuo to give 1.60 g (75%) of the titled compound.

Physical data are shown in Table IX.

The compounds shown in Table IX are prepared by the similar method described above using corresponding amine derivatives.

TABLE I

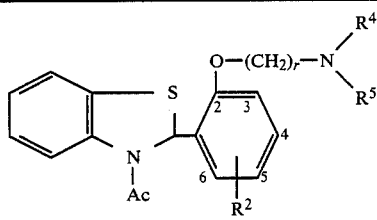

| Compd. No. | $R^2$ | $R^4$ | $R^5$ | r | Method of prepn. (Examp. No.) | Yield (%) | mp (°C.) (Recrystn. solvent) | IR(KBr, cm$^{-1}$) |
|---|---|---|---|---|---|---|---|---|
| 1*[1] | H | H | H | 3 | 4 | 65 | 106–109 (dec.) | 3400, 1660, 1466, 1382, 1232, 748 |
| 2*[2] | H | H | —CH$_3$ | 3 | 6 | 65 | 111–113 | 3420, 1674, 1458, 1370, 724, 616 |
| 3*[1] | H | H | —C(CH$_3$)$_3$ | 4 | 5 | 75 | 193–195 | 3500, 3430, 2950, 2770, 1667, 1585, 1455, 1371, 1320, 1266, 1221, 1095, 741 |
| 4*[1] | H | H | —CHPh(CH$_2$Ph) | 3 | 5 | 75 | 235.5–238.0 (dec.) | 3020, 2940, 1678, 1598, 1488, 1462, 1376, 1244, 1226, 1098, 744 |
| 5*[1] | H | H | —CH$_2$CH$_2$-(3,4-diOCH$_3$-Ph) | 3 | 5 | 70 | 165–169 | 3420, 2940, 1676, 1514, 1462, 1378, 1324, 1262, 1250, 1228, 1022, 746 |
| 6*[1] | H | —CH$_3$ | —CH$_3$ | 2 | 3 | 80 | 209–210 (MeOH—AcOEt) | 3430, 1670, 1460, 1387, 1354, 1325, 1272, 1245, 1230, 1170, 1103, 1050, 1022, 930, 750 |
| 7 | H | —CH$_3$ | —CH$_3$ | 3 | 3 | 56 | 92.5–94.5 ((Me$_2$CH)$_2$O—hexane) | 1678, 1600, 1466, 1376, 1312, 1274, 1246, 1218, 1006, 746 |
| 8*[1] | H | —CH$_3$ | cyclohexyl | 3 | 5 | 75 | 130–142 (MeOH—AcOEt) | 3400, 2930, 2910, 1672, 1464, 1380, 1322, 1272, 1242, 1224, 750 |
| 9*[3] | H | —CH$_3$ | —CH$_2$Ph | 3 | 5 | 80 | 159–162 | 3450, 1676, 1580, 1490, 1466, 1380, 750, 702 |
| 10*[1] | H | —CH$_2$CH$_3$ | —CH$_2$CH$_3$ | 3 | 5 | 80 | 154–156 (MeOH—AcOEt) | 3480, 3420, 2930, 1676, 1462, 1378, 1320, 1270, 1240, 1224, 1098, 752 |
| 11*[1] | H | —CH$_2$CH$_3$ | —CH$_2$CH$_3$ | 4 | 5 | 80 | amorph. | 3420, 1665, 1465, 1380, 1324, 1270, 1230, 748 |
| 12*[1] | H | cyclohexyl | cyclohexyl | 3 | 5 | 65 | amorph. | 2940, 2870, 1684, 1468, 1380, 750 |
| 13*[1] | H | —CH$_2$CH$_2$OH | —CH$_2$CH$_2$OH | 3 | 9 | 60 | 145–149 | 3320, 1666, 1466, 1380, 1314, 1236, 748 |
| 14*[1] | 3-OCH$_3$ | —CH$_3$ | —CH$_3$ | 3 | 3 | 70 | 221–222 (MeOH) | 3410, 1665, 1580, 1465, 1375, 1343, 1270, 1232, 1060, 1030, 753, 740 |
| 15*[1] | 3-OCH$_3$ | —CH$_3$ | —CH$_3$ | 4 | 5 | 65 | 199–200 | 3420, 2930, 1675, 1575, 1460, 1375, 1268, 753, 740 |
| 16*[3] | 3-OCH$_3$ | —CH$_3$ | cyclohexyl | 3 | 5 | 70 | amorph. | 3400, 2930, 1710, 1665, 1575, 1460, 1370, 1268, 1055, 745 |

TABLE I-continued

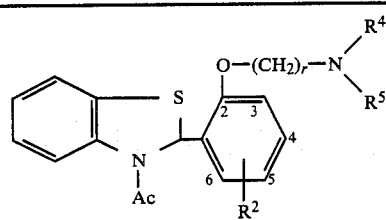

| Compd. No. | R² | R⁴ | R⁵ | r | Method of prepn. (Examp. No.) | Yield (%) | mp (°C.) (Recrystn. solvent) | IR(KBr, cm⁻¹) |
|---|---|---|---|---|---|---|---|---|
| 17*¹ | 3-OCH₃ | —CH₃ | —⟨H⟩ | 4 | 5 | 60 | 197–198 | 3550, 3460, 2950, 1675, 1660, 1482, 1466, 1380, 1272, 1055, 775, 750 |
| 18*³ | 5-OCH₃ | —CH₃ | —CH₃ | 3 | 3 | 73 | 165.5–166 (MeOH) | 3430, 1672, 1580, 1492, 1465, 1373, 1207, 1053, 870, 749 |
| 19*⁴ | 5-OCH₃ | —CH₃ | —⟨H⟩ | 3 | 5 | 80 | 191.5–192 (dec.) (CH₃CN—MeOH) | 3420, 3180, 2860, 1769, 1670, 1498, 1460, 1380, 1368, 1300, 1280, 1209, 1060, 750, 715 |
| 20*⁴ | 5-OCH₃ | —CH₃ | —⟨H⟩ | 4 | 5 | 60 | 147–148 (CH₃CN) | 3420, 1670, 1493, 1463, 1372, 1275, 1240, 1208, 1037, 743, 720 |
| 21*² | 5-OCH₃ | —CH₃ | —⟨H⟩ | 5 | 7 | 70 | 155.5–157.5 | 3420, 2930, 1670, 1466, 1380, 1275, 1207 |
| 22*⁴ | 5-OCH₃ | —CH₃ | —⟨H⟩ | 6 | 7 | 55 | 135–137 | 3440, 1675, 1493, 1465, 1380, 1280, 1210, 1040, 750, 720, 700 |
| 23*¹ | 5-OCH₃ | —CH₃ | —CH₂CH₂—⟨OCH₃/OCH₃⟩ | 4 | 9 | 80 | amorph. | 3424, 1664, 1493, 1463, 1377, 1321, 1272, 1262, 1236, 1208, 1155, 1028 748 |
| 24*¹ | 5-OCH₃ | —⟨H⟩ | —CH₂CH₂OH | 4 | 9 | 70 | amorph. | 3336, 1664, 1493, 1464, 1397, 1274, 1208, 1036, 748 |
| 25*¹ | 5-OCH₃ | —⟨H⟩ | —CH₂CH₂—⟨OCH₃/OCH₃⟩ | 4 | 9 | 75 | amorph. | 3424, 1668, 1510, 1496, 1466, 1272, 1262, 1237, 1208, 1025, 750 |
| 26*¹ | 5-Cl | —CH₃ | —CH₃ | 3 | 3 | 70 | 193–195.5 ((Me₂CH)₂O—Et₂O) | 3420, 1678, 1466, 1376, 1226 1110, 1035, 764 |
| 27*¹ | 3-NO₂ | —CH₃ | —⟨H⟩ | 3 | 5 | 70 | 103–106 | 3420, 1668, 1598, 1528, 1464, 1376, 1348, 1319, 1270, 1225, 742 |
| 28*² | 5-NO₂ | —CH₃ | —CH₃ | 3 | 3 | 65 | 159–160 (dec.) (MeOH—CH₃CN) | 3420, 1670, 1610, 1591, 1515, 1463, 1379, 1340, 1268, 1225, 1078, 1032, 980, 745 |
| 29*² | 5-NO₂ | —CH₃ | —⟨H⟩ | 3 | 5 | 55 | 168–169 (dec.) (MeOH—CH₃CN) | 3460, 1693, 1670, 1588, 1512, 1461, 1375, 1336, 1265, 1212 1074, 741 |

TABLE I-continued

| Compd. No. | R² | R⁴ | R⁵ | r | Method of prepn. (Examp. No.) | Yield (%) | mp (°C.) (Recrystn. solvent) | IR(KBr, cm⁻¹) |
|---|---|---|---|---|---|---|---|---|
| 30*² | 5-NO₂ | —CH₃ | ⟨H⟩ cyclohexyl | 4 | 5 | 60 | 176.5–178 (dec.) (MeOH—CH₃CN) | 3420, 1695, 1591, 1510, 1465, 1379, 1341, 1267, 1226, 1079, 755 |
| 31*² | 5-NO₂ | —CH₃ | ⟨H⟩ cyclohexyl | 5 | 7 | 70 | 172–174 (dec.) (MeOH—CH₃CN) | 3430, 1710, 1675, 1591, 1511, 1467, 1380, 1336, 1265, 1230, 1078, 982, 747 |
| 32*² | 5-NO₂ | —CH₃ | ⟨H⟩ cyclohexyl | 6 | 7 | 70 | 178–180 (dec.) (MeOH—CH₃CN) | 3430, 1715, 1679, 1591, 1511, 1461, 1377, 1335, 1268, 1227, 1077, 982, 749 |
| 33*⁵ | 5-NO₂ | H | —CH₂-pyridyl | 3 | 9 | 55 | 83–85 (AcOEt) | 3400, 3290, 1678, 1612, 1592, 1580, 1522, 1466, 1348, 1338, 1268, 1080, 748 |
| 34*² | 3-OCH₃ 5-NO₂ | —CH₃ | ⟨H⟩ cyclohexyl | 3 | 5 | 65 | 157–159 (MeOH—CH₃CN) | 3420, 1705, 1677, 1570, 1530, 1463, 1370, 1340, 1294, 1273 1213, 1194, 1162, 1062, 981, 763, 738 |

*¹Hydrochloride
*²Fumarate
*³Maleate
*⁴Oxalate
*⁵Monohydrate

TABLE II

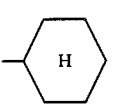

| Compd. No. | R² | R⁴ | R⁵ | r | Method of prepn. (Examp. No.) | Yield (%) | mp(°C.) (Recrystn. solvent) | IR(KBr, cm⁻¹) |
|---|---|---|---|---|---|---|---|---|
| 35*¹ | H | —CH₃ | —CH₃ | 3 | 3 | 70 | 162–164 | 3420, 1716, 1680, 1606, 1586, 1463, 1381, 1306, 1288, 954 |
| 36 | 4-OH | —CH₃ | —CH₃ | 3 | 8 | 30 | oil | 3340, 1675, 1585, 1510, 1480 1430, 1300, 1270, 1141, 750 (neat) |
| 37*¹ | 4-OH | —CH₃ | ⟨H⟩ cyclohexyl | 3 | 8 | 50 | 130–133 (dec.) | 3400, 1670, 1575, 1510, 1462, 1430, 1375, 1340, 1320, 1272, 1230, 1208, 985, 745 |

TABLE II-continued

[Structure: benzothiazoline with N-Ac, S-CH linked to phenyl ring bearing R² (at position 5/6) and O-(CH₂)ᵣ-NR⁴R⁵ at position 3]

| Compd. No. | R² | R⁴ | R⁵ | r | Method of prepn. (Examp. No.) | Yield (%) | mp(°C.) (Recrystn. solvent) | IR(KBr, cm$^{-1}$) |
|---|---|---|---|---|---|---|---|---|
| 38*² | 4-OCH₃ | —CH₃ | cyclohexyl | 4 | 5 | 85 | amorph. | 3400, 1660, 1512, 1460, 1380, 1340, 1255, 1135, 1020, 750 |
| 39*² | 4-NO₂ | —CH₃ | cyclohexyl | 3 | 5 | 70 | 115–117 | 3420, 1662, 1606, 1513, 1464, 1375, 1343, 1314, 1272, 745 |
| 40*² | 6-NO₂ | —CH₃ | cyclohexyl | 3 | 5 | 65 | 69–73 | 3430, 1665, 1610, 1580, 1510, 1468, 1378, 1318, 1290, 1226, 748 |

*¹Fumarate
*²Hydrochloride

TABLE III

[Structure: benzothiazoline with N-Ac, S-CH linked to phenyl ring bearing R² (at position 5/6) and O-(CH₂)ᵣ-NR⁴R⁵ at position 4]

| Compd. No. | R² | R⁴ | R⁵ | r | Method of prepn. (Examp. No.) | Yield (%) | mp(°C.) (Recrystn. solvent) | IR(KBr, cm$^{-1}$) |
|---|---|---|---|---|---|---|---|---|
| 41*¹ | H | —CH₃ | —CH₃ | 2 | 3 | 80 | amorph. | 3410, 1664, 1510, 1464, 1378, 1234, 748 |
| 42*¹ | H | —CH₃ | —CH₃ | 3 | 3 | 75 | oil | 3400, 1660, 1610, 1580, 1460, 1380, 1230, 1174, 750 (neat) |
| 43*¹ | H | —CH₃ | —CH₃ | 4 | 5 | 80 | amorph. | 3420, 2940, 1666, 1510, 1464, 1376, 1244, 1174, 748 |
| 44*¹ | H | —CH₃ | cyclohexyl | 3 | 5 | 75 | amorph. | 3420, 2930, 1684, 1510, 1462, 1376, 1326, 1268, 1244, 1230, 1174, 748 |
| 45*¹ | H | —CH₃ | cyclohexyl | 4 | 5 | 75 | amorph. | 3420, 2940, 1666, 1510, 1464, 1376, 1328, 1270, 1244, 1174, 748 |
| 46*¹ | H | —CH₂CH₃ | —CH₂CH₃ | 3 | 5 | 75 | amorph. | 3420, 2930, 1662, 1506, 1460, 1374, 1324, 1266, 1238, 1172, 748 |
| 47 | 3-OH | —CH₃ | cyclohexyl | 3 | 8 | 40 | oil | 3330, 1666, 1575, 1502, 1461, 1376, 1340, 1270, 1216, 1121, 1025, 745 (neat) |
| 48*¹ | 3-OCH₃ | —CH₃ | —CH₃ | 3 | 3 | 80 | amorph. | 3420, 1662, 1510, 1460, 1375, 1335, 1256, 1230, 1132, 1025, 746 |

TABLE III-continued

| Compd. No. | R² | R⁴ | R⁵ | r | Method of prepn. (Examp. No.) | Yield (%) | mp(°C.) (Recrystn. solvent) | IR(KBr, cm⁻¹) |
|---|---|---|---|---|---|---|---|---|
| 49*¹ | 3-OCH₃ | —CH₃ | —CH₃ | 4 | 5 | 70 | amorph. | 3420, 1665, 1510, 1462, 1375, 1255, 1230, 1132, 1025, 750 |
| 50*¹ | 3-OCH₃ | —CH₃ | cyclohexyl(H) | 3 | 5 | 75 | amorph. | 3420, 1666, 1512, 1465, 1378, 1255, 1230, 1135, 1027, 750 |
| 51*¹ | 3-OCH₃ | —CH₃ | cyclohexyl(H) | 4 | 5 | 70 | amorph. | 3400, 1663, 1510, 1460, 1378, 1255, 1132, 1025, 746 |
| 52*¹ | 3-NO₂ | —CH₃ | cyclohexyl(H) | 3 | 5 | 75 | amorph. | 3420, 1665, 1618, 1530, 1463, 1376, 1350, 1320, 1270, 1081, 1027, 749 |
| 53*¹ | 3-OCH₃, 5-OCH₃ | —CH₃ | —CH₃ | 3 | 5 | 65 | amorph. | 3410, 2940, 1656, 1582, 1452, 1412, 1368, 1318, 1220, 1112, 740 |
| 54*¹ | 3-OCH₃, 5-OCH₃ | —CH₃ | cyclohexyl(H) | 3 | 5 | 60 | amorph. | 3440, 2950, 1664, 1588, 1462, 1420, 1380, 1338, 1236, 1124, 752 |
| 55*¹ | 3-OCH₃, 5-OCH₃ | —CH₃ | cyclohexyl(H) | 4 | 5 | 75 | amorph. | 3420, 2932, 1664, 1589, 1458, 1419, 1379, 1327, 1271, 1229, 1122 |

*¹Hydrochloride

TABLE IV

| Compd. No. | R² | R⁶ | r | Method of prepn. (Examp. No.) | Yield (%) | mp (°C.) (Recrystn. solvent) | IR(KBr, cm⁻¹) |
|---|---|---|---|---|---|---|---|
| 56*¹ | H | —CH₃ | 3 | 3 | 65 | 213–215 | 3400, 1664, 1460, 1376, 1322, 1272, 1226, 746 |
| 57*² | H | —CH₂CH₂—C₆H₃(OCH₃)₂ (3,4-diOCH₃) | 2 | 9 | 80 | 181–182 (dec.) (MeOH—CH₃CN) | 3430, 1683, 1615, 1573, 1513, 1460, 1375, 1352, 1319, 1259, 1222, 1095, 1022, 860, 755 |
| 58*² | H | —CH₂CH₂—C₆H₃(OCH₃)₂ (3,4-diOCH₃) | 3 | 9 | 70 | 172–173 (dec.) (MeOH—CH₃CN) | 3430, 1687, 1619, 1570, 1515, 1460, 1378, 1352, 1321, 1260, 1238, 1225, 1098, 1024, 864, 755, 743 |

TABLE IV-continued

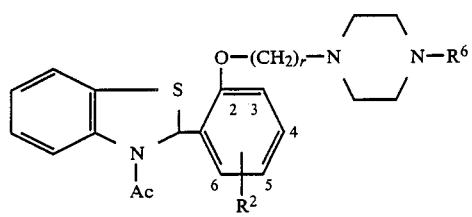

| Compd. No. | $R^2$ | $R^6$ | r | Method of prepn. (Examp. No.) | Yield (%) | mp (°C.) (Recrystn. solvent) | IR(KBr, cm$^{-1}$) |
|---|---|---|---|---|---|---|---|
| 59*3 | H | —COCH$_2$—C$_6$H$_3$(OCH$_3$)$_2$ | 2 | 9 | 60 | 144–146 (dec.) (MeOH—CH$_3$CN) | 3430, 1705, 1682, 1651, 1586, 1511, 1459, 1374, 1263, 1223, 1152, 1022, 751 |
| 60*3 | H | —COCH$_2$—C$_6$H$_3$(OCH$_3$)$_2$ | 3 | 9 | 75 | 149–151 (dec.) (CH$_3$CN) | 3420, 1712, 1679, 1647, 1590, 1513, 1460, 1375, 1262, 1227, 11155 1023, 975, 750 |
| 61*4 | H | —COCH=CH—(E)—C$_6$H$_3$(OCH$_3$)$_2$ | 3 | 9 | 85 | 131–132 (dec.) (MeOH—Et$_2$O) | 3420, 1670, 1640, 1585, 1512, 1459, 1374, 1260, 1138, 1022, 740 |
| 62*2 | 5-OCH$_3$ | —CH$_2$CH$_2$—C$_6$H$_3$(OCH$_3$)$_2$ | 3 | 9 | 60 | 181–182 (dec.) (MeOH—CH$_3$CN) | 3430, 1671, 1618, 1572, 1492, 1462, 1377, 1353, 1322, 1260, 1236, 1207, 1155, 1099, 1025, 862, 745 |
| 63*5 | 5-OCH$_3$ | —CH$_2$CH$_2$—C$_6$H$_3$(OCH$_3$)$_2$ | 4 | 9 | 65 | 197.5–198.5 (MeOH—CH$_3$CN) | 3420, 1708, 1668, 1575, 1495, 1461, 1373, 1295, 1267, 1233, 1205, 1152, 1022, 973, 743 |
| 64*2 | 5-OCH$_3$ | —CH$_2$CH$_2$—C$_6$H$_3$(OCH$_3$)$_2$ | 5 | 9 | 70 | 195.5–197.5 (dec.) | 3440, 1664, 1580, 1500, 1466, 1381, 1208, 1023, 865 |
| 65*2 | 5-OCH$_3$ | —CH$_2$CH$_2$—C$_6$H$_3$(OCH$_3$)$_2$ | 6 | 9 | 60 | 188–189 (MeOH—CH$_3$CN) | 3430, 1670, 1618, 1570, 1465, 1380, 1354, 1260, 1240, 1210, 1027, 865 |
| 66*2 | 5-OCH$_3$ | —CH$_2$CH$_2$OH | 4 | 9 | 80 | 186–187 (dec.) (MeOH—CH$_3$CN) | 3480, 1700, 1672, 1620, 1575, 1490, 1468, 1380, 1359, 1276, 1210, 1070, 865, 746 |
| 67*1 | 5-OCH$_3$ | —CH$_2$CH$_2$—C$_6$H$_2$(OCH$_3$)$_3$ | 4 | 9 | 60 | 239–240 (dec.) | 3420, 1674, 1588, 1500, 1460, 1420, 1376, 1232, 1212, 1120, 1040, 758 |
| 68*2 | 5-OCH$_3$ | —CH$_2$—C$_6$H$_2$(OCH$_3$)$_3$ | 4 | 9 | 80 | 175–177 (EtOH—CH$_3$CN) | 3430, 1664, 1571, 1492, 1465, 1379, 1360, 1277, 1208, 1102, 1062, 864 |
| 69*5 | 5-OCH$_3$ | —CH(C$_6$H$_5$)(C$_6$H$_4$Cl) | 4 | 9 | 70 | 170–173 | 3440, 1491, 1465, 1379, 1274, 1209, 752 |
| 70*2 | 5-OCH$_3$ | —CH$_2$CH$_2$OCO—C$_6$H$_2$(OCH$_3$)$_3$ | 4 | 9 | 75 | 181–182.5 (dec.) (MeOH—CH$_3$CN) | 3450, 1710, 1672, 1580, 1466, 1378, 1355, 1330, 1210, 1123, 862, 746 |

TABLE IV-continued

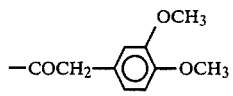

| Compd. No. | $R^2$ | $R^6$ | r | Method of prepn. (Examp. No.) | Yield (%) | mp (°C.) (Recrystn. solvent) | IR(KBr, cm$^{-1}$) |
|---|---|---|---|---|---|---|---|
| 71[*3] | 5-OCH$_3$ | —COCH$_2$—C$_6$H$_3$(OCH$_3$)$_2$ | 3 | 9 | 65 | 130–131 (dec.) (AcOEt) | 3420, 1701, 1660, 1641, 1590, 1515, 1499, 1463, 1372, 1272, 1260, 1231, 1207, 1140, 1023, 980, 750 |
| 72[*6] | 5-OCH$_3$ | —COCH=CH—C$_6$H$_3$(OCH$_3$)$_2$ (E) | 3 | 9 | 70 | 175–176 (dec.) (CH$_3$CN) | 3430, 1641, 1580, 1509, 1462, 1373, 1260, 1207, 1136, 1022, 975, 863, 745 |
| 73[*2] | 5-NO$_2$ | —(CH$_2$)$_7$CH$_3$ | 3 | 9 | 75 | 176.5–177.5 (MeOH—CH$_3$CN) | 3420, 1676, 1610, 1580, 1510, 1468, 1380, 1342, 1272, 1080, 865, 748 |
| 74[*2] | 5-NO$_2$ | —CH$_2$CH$_2$—C$_6$H$_3$(OCH$_3$)$_2$ | 3 | 9 | 90 | 156.5–158 (dec.) (MeOH—CH$_3$CN) | 3420, 1660, 1573, 1508, 1461, 1378, 1338, 1262, 1231, 1189, 1138, 1075, 1020, 860, 741, 710 |
| 75[*7] | 5-NO$_2$ | —CO(CH$_2$)$_6$CH$_3$ | 3 | 9 | 70 | 90–92.5 (CHCl$_3$—Et$_2$O) | 3450, 1650, 1590, 1466, 1340, 1270, 748, 712 |
| 76[*2] | 5-NO$_2$ | —CH$_2$CO—C$_6$H$_5$ | 3 | 9 | 75 | 144–145 (dec.) | 3410, 1661, 1572, 1508, 1462, 1378, 1337, 1267, 1225, 1074, 1011, 860, 741 |
| 77[*2] | 5-NO$_2$ | —CH$_2$CH(OH)—C$_6$H$_5$ | 3 | 9 | 70 | 153–155 (dec.) (EtOH) | 392, 1654, 1576, 1508, 1465, 1381, 1340, 1270, 1192, 1077, 1013, 863, 745, 701 |
| 78[*8] | 5-NO$_2$ | —CH$_2$CO—C$_6$H$_4$—OH | 3 | 9 | 75 | 199–202 (dec.) (DMSO—H$_2$O) | 3400, 1663, 1647, 1597, 1510, 1463, 1398, 1380, 1339, 1271, 1225, 1168, 718 |
| 79[*4] | 5-NO$_2$ | —CO—(2-furyl) | 3 | 9 | 80 | 181–183 (dec.) (MeOH—CH$_3$CN) | 3492, 3400, 1671, 1618, 1593, 1513, 1484, 1466, 1384, 1339, 1273, 1229, 1080, 759, 742 |
| 80[*1] | 3-OCH$_3$ 5-NO$_2$ | —CH$_2$CH$_2$—C$_6$H$_3$(OCH$_3$)$_2$ | 3 | 9 | 75 | 147–150 (dec.) (MeOH—H$_2$O) | 3410, 1662, 1514, 1460, 1374, 1338, 1291, 1236, 1139, 1098, 1060, 1021, 951, 747 |

[*1] Dihydrochloride
[*2] Dimaleate
[*3] Fumarate
[*4] Hydrochloride
[*5] Difumarate
[*6] Maleate
[*7] Oxalate
[*8] Dioxalate

TABLE V

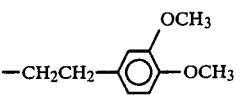

| Compd. No. | $R^2$ | $R^6$ | r | Method of prepn. (Examp. No.) | Yield (%) | mp (°C.) (Recrystn. solvent) | IR(KBr, cm$^{-1}$) |
|---|---|---|---|---|---|---|---|
| 81* | 4-OCH$_3$ | —CH$_2$CH$_2$—(2,3-diOCH$_3$-C$_6$H$_3$) | 4 | 9 | 85 | 168–169 (MeOH—CH$_3$CN) | 3450, 1682, 1620, 1580, 1515, 1460, 1375, 1359, 1336, 1260, 1240, 1139, 1027, 865, 745 |

*Dimalate

TABLE VI

| Compd. No. | $R^2$ | $R^6$ | r | Method of prepn. (Examp. No.) | Yield (%) | mp(°C.) (Recrystn. solvent) | IR(KBr, cm$^{-1}$) |
|---|---|---|---|---|---|---|---|
| 82*[1] | H | —CH$_2$CH$_2$—(2,3-diOCH$_3$-C$_6$H$_3$) | 3 | 9 | 60 | 175–177 (dec.) (MeOH—CH$_3$CN) | 3420, 1712, 1660, 1575, 1509, 1462, 1373, 1300, 1260, 1233, 1171, 1024, 970, 757 |
| 83*[2] | 3-OCH$_3$ | —CH$_2$CH$_2$—(2,3-diOCH$_3$-C$_6$H$_3$) | 3 | 9 | 85 | 164–165 (MeOH—CH$_3$CN) | 3430, 1665, 1619, 1570, 1510, 1460, 1375, 1353, 1325, 1256, 1235, 1132, 1025, 865 |
| 84*[2] | 3-OCH$_3$ | —CH$_2$CH$_2$—(2,3-diOCH$_3$-C$_6$H$_3$) | 4 | 9 | 80 | 167–168 (MeOH—CH$_3$CN) | 3430, 1670, 1570, 1450, 1370, 1355, 1325, 1255, 1240, 1130, 1025, 865, 750 |
| 85*[2] | 3-OCH$_3$ 5-OCH$_3$ | —CH$_2$CH$_2$—(2,3-diOCH$_3$-C$_6$H$_3$) | 4 | 9 | 70 | 163.5–165.5 | 3450, 1670, 1577, 1499, 1460, 1379, 1328, 1261, 1236, 1122, 1024, 866 |

*[1]Difumarate
*[2]Dimaleate

TABLE VII
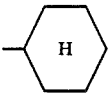
| Compd. No. | R⁴ | R⁵ | Method of prepn. (Examp. No.) | Yield (%) | mp(°C.) (Recrystn. solvent) | IR(KBr, cm⁻¹) |
|---|---|---|---|---|---|---|
| 86* | H | —C(CH₃)₃ | 1, 2 | 81 | 188–192 (CHCl₃—Et₂O) | 3350, 2980, 2790, 1672, 1660, 1470, 1384, 1224, 750 |
| 87a* | —CH₃ | 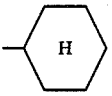 | 1 | 35 | 208–210 | 3225, 2940, 1686, 1464, 1382, 744 |
| 87b* | —CH₃ |  | 1 | 30 | 143–146 | 3350, 2940, 1672, 1464, 1382, 748 |
| 88* | —CH₂CH₃ | —CH₂CH₃ | 1 | 75 | amorph. | 3400, 2930, 1658, 1600, 1460, 1380, 1326, 1274, 1234, 1102, 1028, 750 |
*Hydrochloride
Compound 87a is the diastereoisomer of compound 87b.
TABLE VIII
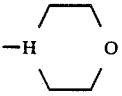
| Compd. No. | R² | R⁹ | r | Method of prepn. (Examp. No.) | Yield (%) | mp(°C.) (Recrystn. solvent) | IR(KBr, cm⁻¹) |
|---|---|---|---|---|---|---|---|
| 89*¹ | H | 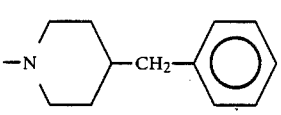 | 3 | 5 | 70 | 124–127 | 3430, 2940, 1674, 1466, 1380, 746 |
| 90 | H | 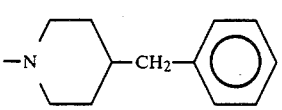 | 3 | 3 | 55 | 121–122.5 | 1676, 1466, 1456, 1374, 1324, 1276, 1252, 1230, 1116, 752 |
| 91*² | H | 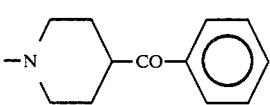 | 3 | 9 | 75 | 184–186 (dec.) | 3450, 1728, 1685, 1605, 1465, 1384, 1280, 1254, 1239, 758 |
| 92*² | 5-OCH₃ | 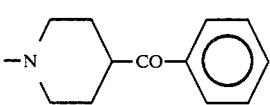 | 4 | 9 | 70 | 148–150 (iso-PrOH—AcOEt—Et₂O) | 3420, 1705, 1669, 1493, 1463, 1379, 1320, 1275, 1237, 1207, 1140, 745 |
| 93*³ | 5-OCH₃ | 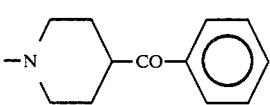 | 4 | 9 | 80 | 182–184 (MeOH—CH₃CN) | 3450, 1720, 1671, 1595, 1461, 1378, 1278, 1208, 702 |

TABLE VIII-continued

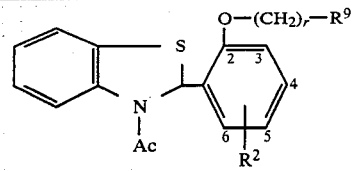

| Compd. No. | R² | R⁹ | r | Method of prepn. (Examp. No.) | Yield (%) | mp(°C.) (Recrystn. solvent) | IR(KBr, cm⁻¹) |
|---|---|---|---|---|---|---|---|
| 94*³ | 5-NO₂ | —N⟨piperidine⟩—OH | 3 | 9 | 75 | 175-178 (dec.) (MeOH—CH₃CN) | 3408, 1664, 1610, 1592, 1509, 1459, 1381, 1340, 1270, 1226, 1074, 744, 700 |
| 95*³ | 5-NO₂ | —N⟨piperidine⟩—CH₂—C₆H₅ | 3 | 9 | 70 | 190-191 (dec.) (MeOH—CH₃CN) | 3424, 1718, 1689, 1608, 1594, 1510, 1465, 1376, 1339, 1269, 1195, 744, 701 |

*¹Hydrochloride
*²Fumarate
*³Oxalate

TABLE IX

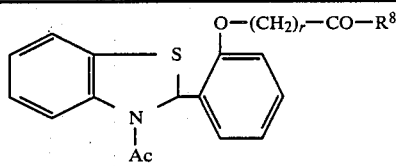

| Compd. No. | R⁸ | r | Method of prepn. (Examp. No.) | Yield (%) | mp(°C.) (Recrystn. solvent) | IR(KBr, cm⁻¹) |
|---|---|---|---|---|---|---|
| 96 | —OH | 3 | 11 | 80 | 121-122.5 (AcOEt—Et₂O—Me₂CHOCHMe₂) | 3420, 1725, 1636, 1465, 1387, 1272, 1242, 1231, 1176, 1100, 1040, 745 |
| 97 | —OCH₂CH₃ | 3 | 10 | 75 | oil | 1735, 1679, 1601, 1491, 1468, 1380, 1325, 1273, 1247, 1230, 1178, 1100, 1028, 730 (neat) |
| 98 | —NHCH₂CH₂—C₆H₃(OCH₃)(OCH₃) | 3 | 12 | 65 | amorph. | 3310, 1650, 1510, 1461, 1375, 1321, 1257, 1230, 1023, 745 |
| 99* | —N⟨piperazine⟩N—CH₃ | 3 | 12 | 80 | 195.5-197 (dec.) (EtOH—H₂O) | 3430, 1652, 1465, 1376, 1328, 1243, 1159, 1022, 975, 747, 642 |
| 100 | —N⟨morpholine⟩O | 3 | 12 | 75 | 133-134 (AcOEt) | 1670, 1639, 1599, 1460, 1373, 1325, 1267, 1227, 1100, 1098, 1028, 750 |

*Fumarate

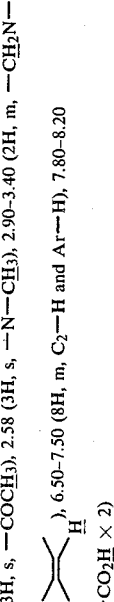

-continued

| No. | | δ (ppm), J = Hz  X NMR |
|---|---|---|
| 9 | DMSO-d₆ | 3.50 (3H, m, —CH₂N—CH⟨ring⟩), 4.21 (2H, t, J = 5.5, —OCH₂—), 6.70–7.50 (8H, m, C₂—H and Ar—H), 7.70–8.10 (1H, m, C₄—H), 10.80–11.50 (1H, br, HCl) |
| | DMSO-d₆ | 2.20–2.50 (2H, m, —OCH₂CH₂CH₂N—), 2.20 (3H, s, —COCH₃), 2.75 (3H, s, —N—CH₃), 3.10–3.50 (2H, m, —CH₂N—), 4.14 (2H, t, J = 5.5, —OCH₂—), 4.35 (2H, s, —NCH₂Ph), 6.05 (2H, s, —NCH₂Ph ⟨=CH—H⟩), 6.70–7.70 (8H, m, C₂—H and Ar—H), 7.47 (5H, s, —NCH₂C₆H₅), 7.70–8.20 (1H, m, C₄—H), 11.00–14.00 (2H, br, —CO₂H × 2) |
| 10 | DMSO-d₆ | 1.32 (6H, t, J = 7.0, —N(CH₂CH₃)₂), 2.00–2.50 (2H, m, —OCH₂CH₂CH₂N—), 2.23 (3H, s, —COCH₃), 2.90–3.50 6H, m, —CH₂N(CH₂CH₃)₂), 4.22 (2H, t, J = 5.5, —OCH₂—), 6.70–7.40 (8H, m, C₂—H and Ar—H), 7.70–8.10 (1H, m, C₄—H), 10.90–11.50 (1H, br, HCl) |
| 11 | DMSO-d₆ | 1.25 (6H, t, J = 7.0, —N(CH₂CH₃)₂), 1.57–2.13 (4H, m, —OCH₂CH₂CH₂CH₂N—), 2.30 (3H, s, —COCH₃), 2.70–3.40 (6H, m, —CH₂N(CH₂CH₃)₂), 3.90–4.33 (2H, m, —OCH₂—), 6.60–7.57 (8H, m, C₂—H and Ar—H), 7.67–8.23 (1H, m, C₄—H), 10.63–11.40 (1H, br, HCl) |
| 12 | DMSO-d₆ | 0.80–2.60 (22H, m, —OCH₂CH₂CH₂N—(⟨(CH₂)₅⟩)₂), 2.23 (3H, s, —COCH₃), 3.10–3.70 (4H, m, —CH₂N—(⟨CH⟩)₂), 3.90–4.50 (2H, m, —OCH₂—), 6.70–7.50 (8H, m, C₂—H and Ar—H), 7.70–8.10 (1H, m, C₄—H), 10.10–10.60 (1H, br, HCl) |
| 13 | DMSO-d₆ | 2.00–2.60 (2H, m, —OCH₂CH₂CH₂N—), 2.21 (3H, s, —COCH₃), 3.10–3.70 (6H, m, —CH₂N(CH₂—)₂, 3.70–4.00 (4H, m, —CH₂OH × 2), 4.17 (2H, t, J = 5.5, —OCH₂—), 4.50–5.20 (2H, br, —OH × 2), 6.60–7.50 (8H, m, C₂—H and Ar—H), 7.70–8.20 (1H, m, C₄—H), 10.00–10.60 (1H, br, HCl) |
| 14 | DMSO-d₆ | 1.93–2.41 (2H, m, —OCH₂CH₂CH₂N—), 2.22 (3H, s, —COCH₃), 2.77 (6H, s, —N(CH₃)₂), 3.06–3.50 (2H, m, —CH₂N—), 3.81 (3H, s, —OCH₃), 4.13 (2H, t, J = 6.0, —OCH₂—), 6.52 (1H, dd, J = 6.0, 3.5, C₄'—H), 6.87–7.40 (6H, m, C₂—H and Ar—H), 7.73–8.16 (1H, m, C₄—H), 10.50–11.73 (1H, br, HCl) |

-continued

| No. | | δ (ppm), J = Hz  X NMR |
|---|---|---|
| 15 | CDCl₃ | 1.60–2.30 (4H, m, —OCH₂CH₂CH₂CH₂N—), 2.23 (3H, s, —COCH₃), 2.83 (6H, br s, —N(CH₃)₂), 2.80–3.56 (2H, m, —CH₂N—), 3.84 (3H, s, —OCH₃), 4.00–4.56 (2H, m, —OCH₂—), 6.60 (1H, dd, J = 6.0, 3.5, C₄'—H), 6.70–7.30 (6H, m, C₂—H and Ar—H), 7.56–8.30 (1H, m, C₄—H), 11.87–12.80 (1H, br, HCl) |
| 16 | DMSO-d₆ | 0.93–2.30 (12H, m, —OCH₂CH₂CH₂N—⟨(CH₂)₅⟩), 2.17 (3H, s, —COCH₃), 2.75 (3H, s, —NCH₃), 2.97–3.51 (3H, m, —CH₂N—CH⟨H⟩), 3.78 (3H, s, —OCH₃), 4.10 (2H, t, J = 6.0, —OCH₂—), 6.05 (2H, s, ⟨H⟩), 6.52 (1H, dd, J = 6.0, 3.5, C₄'—H), 6.63–7.27 (6H, m, C₂—H and Ar—H), 7.63–8.17 (1H, m, C₄—H), 10.00–14.50 (2H, br, —CO₂H × 2) |
| 17 | CDCl₃ | 0.87–2.23 (14H, m, —OCH₂CH₂CH₂CH₂N—⟨(CH₂)₅⟩), 2.22 (3H, s, —COCH₃), 2.50–2.90 (3H, m, —NCH₃), 2.90–3.53 (3H, m, —CH₂N—CH⟨⟩), 3.83 (3H, s, —OCH₃), 4.00–4.50 (2H, m, —OCH₂—), 6.57 (1H, dd, J = 6.0, 3.5, C₄'—H), 6.57–7.30 (6H, m, C₂—H and Ar—H), 7.57–8.23 (1H, m, C₄—H), 11.40–12.23 (1H, br, HCl) |
| 18 | CDCl₃ | 1.92–2.62 (2H, m, —OCH₂CH₂CH₂N—), 2.25 (3H, s, —COCH₃), 2.88 (6H, s, —N(CH₃)₂), 3.12–3.55 (2H, m, —CH₂N—), 3.62 (3H, s, —OCH₃), 4.12 (2H, t, J = 5.5, —OCH₂—), 6.22 (2H, s, ⟨H⟩), 6.60 (1H, d, J = 2.0, C₆'—H), 6.63–7.30 (6H, m, C₂—H and Ar—H), 7.57–8.30 (1H, m, C₄—H), 12.65–15.50 (2H, br, —CO₂H × 2) |
| 19 | DMSO-d₆ | 0.70–2.10 (12H, m, —OCH₂CH₂CH₂N—⟨(CH₂)₅⟩), 2.21 (3H, s, —COCH₃), 2.70 (3H, s, —NCH₃), 2.90–3.47 (3H, m, —CH₂N—CH⟨⟩), 3.57 (3H, s, —OCH₃), 4.10 (2H, br t, J = 5.5, —OCH₂—), 6.45 (1H, d, J = 2.0, C₆'—H), 6.62–7.37 (6H, m, C₂—H and Ar—H), 7.63–8.20 (1H, m, C₄—H), 9.82 (2H, br s, —CO₂H × 2) |
| 20 | DMSO-d₆ | 0.72–2.12 (14H, m, —OCH₂CH₂CH₂CH₂N—⟨(CH₂)₅⟩), 2.22 (3H, s, —COCH₃), 2.68 (3H, s, —NCH₃), 2.87–3.38 |

-continued

| No. | X NMR δ (ppm), J = Hz |
|---|---|
| 21 DMSO-d$_6$ | (3H, m, —CH$_2$N—CH⟨(CH$_2$)$_5$⟩), 3.57 (3H, s, —OCH$_3$), 3.82–4.35 (2H, m, —OCH$_2$—), 6.48 (1H, d, J = 2.0, C$_6$′—H), 6.62–7.40 (6H, m, C$_2$—H and Ar—H), 9.75 (2H, br s, —CO$_2$H) |
| 22 DMSO-d$_6$ | 0.90–2.20 (16H, m, —OCH$_2$CH$_2$CH$_2$CH$_2$N—⟨(CH$_2$)$_5$⟩), 2.21 (3H, s, —COCH$_3$), 2.53 (3H, s, —NCH$_3$), 2.60–3.40 (3H, m, —CH$_2$N—CH⟨⟩), 3.57 (3H, s, —OCH$_3$), 3.80–4.30 (2H, m, —OCH$_2$—), 6.40–7.50 (7H, m, C$_2$—H and Ar—H), 6.49 (2H, s, ⟨H H⟩), 7.70–8.20 (1H, m, C$_4$—H), 10.20–11.30 (2H, br, —CO$_2$H × 2) |
| 23 DMSO-d$_6$ | 0.73–2.40 (18H, m, —OCH$_2$(CH$_2$)$_4$CH$_2$N—⟨(CH$_2$)$_5$⟩), 2.20 (3H, s, —COCH$_3$), 2.67 (3H, s, —NCH$_3$), 2.80–3.40 (3H, m, —CH$_2$N—CH⟨⟩), 3.57 (3H, s, —OCH$_3$), 3.80–4.23 (2H, m, —OCH$_2$—), 6.43 (1H, d, J = 2.0, C$_6$′—H), 6.63–7.40 (6H, m, C$_2$—H and Ar—H), 7.67–8.20 (1H, m, C$_4$—H), 9.17 (2H, br s, —CO$_2$H × 2) |
| 24 DMSO-d$_6$ | 1.60–2.10 (4H, m, —CH$_2$NCH$_2$CH$_2$CH$_2$—), 2.21 (3H, s, —COCH$_3$), 2.70–2.90 (3H, m, —NCH$_3$), 2.90–3.40 (6H, m, —CH$_2$NCH$_2$CH$_2$—), 3.56 (3H, s, —OCH$_3$(P)), 3.67 (3H, s, —OCH$_3$(A)), 3.71 (3H, s, —OCH$_3$(A)), 3.80–4.20 (2H, m, —OCH$_2$—), 6.45 (1H, d, J = 2.0, C$_6$′—H), 6.60–7.30 (9H, C$_2$—H and Ar—H), 7.70–8.10 (1H, m, C$_4$—H), 10.90–11.50 (1H, br, HCl) |
| | 0.90–2.40 (14H, m, —OCH$_2$CH$_2$CH$_2$CH$_2$N—⟨(CH$_2$)$_5$⟩), 2.20 (3H, s, —COCH$_3$), 2.90–3.60 (5H, m, —CH$_2$N—CH⟨⟩), 3.23 (3H, s, —OCH$_3$(P)), 3.70–4.00 (2H, m, —CH$_2$OH), 3.90–4.30 (2H, m, —OCH$_2$—), 4.67 (1H, s, —OH), 6.41 (1H, d, J = 2.0, C$_6$′—H), 6.70–7.30 (6H, m, C$_2$—H and Ar—H), 7.70–8.20 (1H, m, C$_4$—H), 9.90–10.40 (1H, br, HCl) |
| 25 DMSO-d$_6$ | 0.90–2.40 (14H, m, —OCH$_2$CH$_2$CH$_2$CH$_2$N—⟨(CH$_2$)$_5$⟩), 2.22 (3H, s, —COCH$_3$), 2.90–3.40 (7H, m, —CH$_2$N—CH⟨CH$_2$CH$_2$—⟩), 3.57 (3H, s, —OCH$_3$(P)), 3.65 (3H, s, —OCH$_3$(A)), 3.71 (3H, s, —OCH$_3$(A)), 3.90–4.30 (2H, m, —OCH$_2$—), 6.42 (1H, d, J = 2.0, C$_6$′—H), 6.60–7.20 (9H, m, C$_2$—H and Ar—H), 7.70–8.20 (1H, m, C$_4$—H), 10.90–11.30 |

| No. | X | NMR δ (ppm), J = Hz |
|-----|---|---------------------|
| 26 | DMSO-d₆ | 2.00–2.50 (2H, m, —OCH₂CH₂CH₂N—), 2.28 (1H, s, —COCH₃), 2.76 and 2.83 (6H, each s, —N(CH₃)₂), 3.10–3.68 (2H, m, —CH₂N—), 4.21 (2H, t, J = 5.5, —OCH₂—), 6.80–7.50 (7H, m, C₂—H and Ar—H), 7.70–8.10 (1H, m, C₄—H), 11.00–11.90 (1H, br, HCl) |
| 27 | CDCl₃ | 0.68–2.20 (12H, m, —OCH₂CH₂CH₂N—(CH₂)₅), 2.28 (3H, s, —COCH₃), 2.37 (3H, s, —COCH₃), 2.78 (3H, d, J = 5.0, —NCH₃), 2.80–3.68 (3H, m, —CH₂N—CH), 4.22 (2H, t, J = 5.0, —OCH₂—), 6.67–7.45 (6H, m, C₂—H and Ar—H), 7.50–8.00 (1H, m, C₄—H), 7.77 (1H, dd, J = 8.0, 2.0, C₄′—H), 11.30–12.20 (1H, br, HCl) |
| 28 | DMSO-d₆ | 1.87–2.40 (2H, m, —OCH₂CH₂CH₂N—), 2.28 (3H, s, —COCH₃), 2.62 (6H, s, —N(CH₃)₂), 3.07 (2H, t, J = 7.0, —CH₂N—), 4.32 (2H, t, J = 5.5, —OCH₂—), 6.50 (2H, s, H⟩⟨H), 6.83–7.30 (4H, m, C₂—H, C₅—H, C₆—H and C₇—H), 7.28 (1H, d, J = 9.0, C₃′—H), 7.72 (1H, d, J = 3.0, C₆′—H), 7.83–8.10 (1H, m, C₄—H), 8.15 (1H, dd, J = 9.0, 3.0, C₄′—H), 11.33 (2H, s, —CO₂H × 2) |
| 29 | DMSO-d₆ | 0.85–2.17 (12H, m, —OCH₂CH₂CH₂N—(CH₂)₅), 2.28 (3H, s, —COCH₃), 2.53 (3H, s, —NCH₃), 2.72–3.30 (3H, m, —CH₂N—CH), 4.32 (2H, br t, J = 5.0, —OCH₂—), 6.50 (2H, s, H⟩⟨H), 6.83–7.48 (4H, m, C₂—H, C₅—H, C₆—H and C₇—H), 7.26 (1H, d, J = 9.0, C₃′—H), 7.73 (1H, d, J = 2.5, C₆′—H), 7.80–8.10 (1H, m, C₄—H), 8.17 (1H, dd, J = 9.0, 2.5, C₄′—H), 9.65 (2H, br s, —CO₂H × 2) |
| 30 | DMSO-d₆ | 0.68–2.15 (14H, m, —OCH₂CH₂CH₂N—(CH₂)₅), 2.27 (3H, s, —COCH₃), 2.53 (3H, s, —NCH₃), 2.70–3.23 (3H, m, —CH₂N—CH), 4.00–4.57 (2H, m, —OCH₂—), 6.48 (2H, s, H⟩⟨H), 6.83–7.43 (5H, m, C₂—H, C₅—H, C₆—H, C₇—H and C₃′—H), 7.60–8.20 (1H, m, C₄—H), 7.72 (1H, d, J = 2.5, C₆′—H), 8.15 (1H, dd, J = 9.0, 2.5, C₄′—H), 9.73–10.52 (2H, br, —CO₂H) |

-continued

| No. | X | NMR |
|---|---|---|
| | | δ (ppm), J = Hz |
| 31 | DMSO-d$_6$ | 0.72–2.13 (16H, m, —OCH$_2$(CH$_2$)$_3$CH$_2$N⟨(CH$_2$)$_5$⟩, 2.28 (3H, s, —COCH$_3$), 2.52 (3H, s, —NCH$_3$), 2.67–3.25 (3H, m, —CH$_2$N—CH⟨⟩), 4.25 (2H, br t, J = 5.5, —OCH$_2$—), 6.48 (2H, s, ⟨H⟩C=C⟨H⟩), 6.82–7.48 (5H, m, C$_2$—H, C$_5$—H, C$_6$—H, C$_7$—H and C$_3$'—H), 7.72 (1H, d, J = 2.5, C$_6$'—H), 7.62–8.17 (1H, m, C$_4$'—H), 8.16 (1H, dd, J = 9.0, 2.5, C$_4$'—H), 9.32–10.08 (2H, br, —CO$_2$H) |
| 32 | DMSO-d$_6$ | 0.67–2.18 (18H, m, —OCH$_2$(CH$_2$)$_4$CH$_2$N⟨(CH$_2$)$_5$⟩, 2.28 (3H, s, —COCH$_3$), 2.53 (3H, s, —NCH$_3$), 2.68–3.28 (3H, m, —CH$_2$N—CH⟨⟩), 4.23 (2H, t, J = 5.0, —OCH$_2$—), 6.48 (2H, s, ⟨H⟩C=C⟨H⟩), 6.83–7.47 (5H, m, C$_2$—H, C$_5$—H, C$_6$—H, C$_7$—H and C$_3$'—H), 7.72 (1H, d, J = 2.5, C$_6$'—H), 7.57–8.20 (1H, m, C$_4$'—H), 8.18 (1H, dd, J = 9.0, 2.5, C$_4$'—H), 9.43–10.13 (2H, br, —CO$_2$H × 2) |
| 33 | CDCl$_3$—DMSO-d$_6$ | 2.08 (2H, quintet, J = 6.5, —OCH$_2$CH$_2$CH$_2$N—), 2.28 (3H, s, —COCH$_3$), 2.70 (2H, s, H$_2$O), 2.88 (2H, t, J = 6.5, —CH$_2$N—), 3.83 (2H, s, —NCH$_2$—), 4.30 (2H, t, J = 6.5, —OCH$_2$—), 6.58–7.42 (6H, m, C$_2$—H and Ar—H), 7.48–7.92 (2H, m, C$_4$—H and C$_3$'—H), 7.78 (1H, d, J = 3.0, C$_6$'—H), 8.12 (1H, dd, J = 9.0, 3.0, C$_4$'—H), 8.38 (1H, dd, J = 4.5, 2.0, ⟨pyridine H⟩), 8.52 (1H, d, J = 2.0, ⟨pyridine H⟩) |
| 34 | DMSO-d$_6$ | 0.73–2.15 (12H, m, —OCH$_2$CH$_2$CH$_2$N⟨(CH$_2$)$_5$⟩, 2.27 (3H, s, —COCH$_3$), 2.58 (3H, s, —NCH$_3$), 2.77–3.40 (3H, m, —CH$_2$N—CH⟨⟩), 3.93 (3H, s, —OCH$_3$—), 4.32 (2H, t, J = 5.0, —OCH$_2$—), 6.52 (2H, s, ⟨H⟩C=C⟨H⟩), 6.85–7.33 (4H, m, C$_2$—H, C$_5$—H, C$_6$—H and C$_7$—H), 7.38 (1H, d, J = 2.5, C$_4$'—H), 7.67–8.10 (1H, m, C$_4$'—H), 7.78 (1H, d, J = 2.5, C$_6$'—H), 11.05 (2H, br s, —CO$_2$H × 2) |
| 35 | DMSO-d$_6$ | 1.80–2.40 (2H, m, —OCH$_2$CH$_2$CH$_2$N—), 2.22 (3H, s, —COCH$_3$), 2.53 (6H, s, —N(CH$_3$)$_2$), 2.70–3.10 (2H, m |

-continued

| No. | | δ (ppm), J = Hz |
|---|---|---|
| | | X NMR |
| 36 | CDCl$_3$ | —CH$_2$N—), 3.96 (2H, t, J = 6.0, —OCH$_2$—), 6.49 (2H, s, \>C=C<$^H_H$), 6.70–7.30 (8H, m, C$_2$—H and Ar—H), 7.70–8.10 (1H, m, C$_4$—H), 11.44 (2H, s, —CO$_2$H × 2) |
| 37 | DMSO-d$_6$ | 1.83–2.27 (2H, m, —OCH$_2$CH$_2$CH$_2$N—), 2.18 (3H, s, —COCH$_3$), 2.37 (6H, s, —N(CH$_3$)$_2$), 3.00 (2H, t, J = 6.0, —CH$_2$N—), 4.10 (2H, t, J = 6.0, —OCH$_2$—), 6.77–8.07 (8H, m, C$_2$—H, —OH and Ar—H), 8.17–8.57 (1H, m, C$_4$—H) |
| | | 0.70–2.37 (12H, m, —OCH$_2$CH$_2$CH$_2$N⟨(CH$_2$)$_5$⟩), 2.20 (3H, s, —COCH$_3$), 2.63 (s, —NCH$_3$), 2.87–3.53 (3H, m, —CH$_2$N—CH⟨⟩), 3.70–4.20 (2H, m, —OCH$_2$—), 6.37–7.40 (7H, m, C$_2$—H and Ar—H), 6.58 (2H, s, \>C=C<$^H_H$), 7.70–8.10 (1H, m, C$_4$—H), 10.00–11.37 (3H, br, —CO$_2$H × 2 and —OH) |
| 38 | DMSO-d$_6$ | 0.67–2.17 (14H, m, —OCH$_2$CH$_2$CH$_2$N⟨(CH$_2$)$_5$⟩), 2.20 (3H, s, —COCH$_3$), 2.53–2.73 (3H, m, —NCH$_3$), 2.80–3.40 (3H, m, —CH$_2$N—CH⟨⟩), 3.70 (3H, s, —OCH$_3$), 3.77–4.07 (2H, m, —OCH$_2$—), 6.53–7.40 (7H, m, C$_2$—H and Ar—H), 7.73–8.10 (1H, m, C$_4$—H), 10.47–11.07 (1H, br, HCl) |
| 39 | DMSO-d$_6$ | 0.72–2.40 (12H, m, —OCH$_2$CH$_2$CH$_2$N⟨(CH$_2$)$_5$⟩), 2.26 (3H, s, COCH$_3$), 2.67 (3H, d, J = 5.0, —NCH$_3$), 2.90–3.56 (3H, m, —CH$_2$N—CH⟨⟩), 4.21 (2H, t, J = 5.5, —OCH$_2$—), 6.75–7.53 (6H, m, C$_2$—H and Ar—H), 7.69–8.10 (1H, m, C$_4$—H), 7.78 (1H, d, J = 9.0, C$_5'$—H), 10.71–11.32 (1H, br, HCl) |
| 40 | CDCl$_3$—DMSO-d$_6$ | 0.90–2.30 (12H, m, —OCH$_2$CH$_2$CH$_2$N⟨(CH$_2$)$_5$⟩), 2.33 (3H, s, —COCH$_3$), 2.70 (3H, d, J = 5.0, —NCH$_3$), 2.90–3.53 (3H, m, —CH$_2$N—CH⟨⟩), 4.10 (2H, t, J = 6.0, —OCH$_2$—), 6.67–7.67 (6H, m, C$_2$—H and Ar—H), 7.67–8.10 (1H, m, C$_4$—H), 8.23 (1H, d, J = 9.0, C$_3'$—H), 11.30–12.00 (1H, br, HCl) |

-continued

| No. | X NMR δ (ppm), J = Hz |
|---|---|
| 41 DMSO-d$_6$ | 2.20 (3H, s, —COC$\underline{H}_3$), 2.57 and 2.93 (6H, each s, —N(C$\underline{H}_3$)$_2$), 3.20-3.70 (2H, m, —C$\underline{H}_2$N$\overset{\|}{}$—), 4.38 (2H, t, J = 5.0, —OC$\underline{H}_2$—), 6.90-7.40 (4H, m, C$_2$—H, C$_5$—H, C$_6$—H and C$_7$—H), 6.95 (2H, d, J = 9.0, C$_3'$—H and C$_5'$—H), 7.23 (2H, d, J = 9.0, C$_2'$—H and C$_6'$—H), 7.80-8.10 (1H, m, C$_4$—H), 10.90-11.70 (1H, br, $\underline{H}$Cl) |
| 42 DMSO-d$_6$ | 1.80-2.30 (2H, m, —OCH$_2$C$\underline{H}_2$CH$_2$N—), 2.17 (3H, s, —COC$\underline{H}_3$), 2.65 and 2.71 (6H, each s, —N(C$\underline{H}_3$)$_2$), 2.90-3.40 (2H, m, —C$\underline{H}_2$N$\overset{\|}{}$—), 3.96 (2H, t, J = 6.0, —OC$\underline{H}_2$—), 6.67-7.33 (4H, m, C$_2$—H, C$_5$—H, C$_6$—H and C$_7$—H), 6.80 (2H, d, J = 9.0, C$_3'$—H and C$_5'$—H), 7.12 (2H, d, J = 9.0, C$_2'$—H and C$_6'$—H), 7.60-8.00 (1H, m, C$_4$—H), 11.00-11.60 (1H, br, $\underline{H}$Cl) |
| 43 DMSO-d$_6$ | 1.60-2.03 (4H, m, —OCH$_2$C$\underline{H}_2$CH$_2$CH$_2$N—), 2.20 (3H, s, —COC$\underline{H}_3$), 2.67-2.72 (6H, each s, —N(C$\underline{H}_3$)$_2$), 4.80-3.40 (2H, m, —C$\underline{H}_2$N$\overset{\|}{}$—), 3.80-4.20 (2H, m, —OC$\underline{H}_2$—), 6.80-7.30 (4H, m, C$_2$—H, C$_5$—H, C$_6$—H and C$_7$—H), 6.82 (2H, d, J = 8.5, C$_3'$—H and C$_5'$—H), 7.29 (2H, d, J = 8.5, C$_2'$—H and C$_6'$—H), 7.70-8.10 (1H, m, C$_4$—H), 10.80-11.50 (1H, br, $\underline{H}$Cl) |
| 44 DMSO-d$_6$ | 1.00-2.50 (12H, m, —OCH$_2$CH$_2$CH$_2$N$\overset{\|}{}$—(C$\underline{H}_2$)$_5$), 2.18 (3H, s, —COC$\underline{H}_3$), 2.58-2.67 (3H, m, —NC$\underline{H}_3$), 2.80-3.40 (3H, m, —C$\underline{H}_2$N—C$\underline{H}$⟨⟩), 4.00 (2H, t, J = 6.0, —OC$\underline{H}_2$—), 6.90-7.30 (4H, m, C$_2$—H, C$_5$—H, C$_6$—H and C$_7$—H), 6.81 (2H, d, J = 9.0, C$_3'$—H and C$_5'$—H), 7.15 (2H, d, J = 9.0, C$_2'$—H and C$_6'$—H), 7.70-8.00 (1H, m, C$_4$—H), 10.70-11.30 (1H, br, $\underline{H}$Cl) |
| 45 DMSO-d$_6$ | 0.90-2.30 (14H, m, —OCH$_2$CH$_2$CH$_2$CH$_2$N$\overset{\|}{}$—(C$\underline{H}_2$)$_5$), 2.18 (3H, s, —COC$\underline{H}_3$), 2.50-2.77 (3H, m, —NC$\underline{H}_3$), 2.80-3.40 (3H, m, —C$\underline{H}_2$N—C$\underline{H}$⟨⟩), 3.70-4.10 (2H, m, —OC$\underline{H}_2$—), 6.78 (2H, d, J = 8.5, C$_3'$—H and C$_5'$—H), 6.80-7.30 (4H, m, C$_2$—H, C$_5$—H, C$_6$—H and C$_7$—H), 7.21 (2H, d, J = 8.5, C$_2'$—H and C$_6'$—H), 7.70-8.10 (1H, m, C$_4$—H), 10.50-11.20 (1H, br, $\underline{H}$Cl) |
| 46 DMSO-d$_6$ | 1.23 (6H, t, J = 7.0, —N(CH$_2$C$\underline{H}_3$)$_2$), 1.90-2.40 (2H, m, —OCH$_2$C$\underline{H}_2$CH$_2$N—), 2.19 (3H, s, —COC$\underline{H}_3$), 2.80-3.40 (6H, m, —C$\underline{H}_2$N(C$\underline{H}_2$CH$_3$)$_2$), 4.03 (2H, t, J = 6.0, —OC$\underline{H}_2$—), 6.80-7.40 (4H, m, C$_2$—H, C$_5$—H, C$_6$—H and C$_7$—H), 6.83 (2H, d, J = 8.5, C$_3'$—H and C$_5'$—H), 7.16 (2H, d, J = 8.5, C$_2'$—H and C$_6'$—H), 7.70-8.00 (1H, m, C$_4$—H), 10.70-11.30 (1H, br, $\underline{H}$Cl) |

-continued

| No. | | δ (ppm), J = Hz X NMR |
|---|---|---|
| 47 | CDCl₃ | 0.67-2.13 (12H, m, -OCH₂CH₂CH₂N$\underset{|}{\frown}$(CH₂)₅$\frown$), 2.22 (3H, s, -COCH₃), 2.25 (3H, s, -NCH₃), 2.37-2.80 (1H, m, -N-C$\underline{H}$$\frown$), 2.70 (2H, t, J = 6.0, -C$\underline{H}$₂N-), 3.90 (2H, t, J = 6.0, -OC$\underline{H}$₂-), 6.43-7.33 (7H, m, C₂-H and Ar-H), 7.57-8.10 (1H, m, C₄-H), 8.83-9.30 (1H, br, -OH) |
| 48 | DMSO-d₆ | 1.73-2.37 (2H, m, -OCH₂C$\underline{H}$₂CH₂N-), 2.20 (3H, s, -COCH₃), 2.57-2.87 (6H, m, -N(C$\underline{H}$₃)₂), 2.93-3.43 (2H, m, -C$\underline{H}$₂N-), 3.67 (3H, s, -OCH₃), 3.96 (2H, t, J = 6.0, -OC$\underline{H}$₂-), 6.53-7.50 (7H, m, C₂-H and Ar-H), 7.70-8.10 (1H, m, C₄-H), 10.77-11.50 (1H, br, $\underline{H}$Cl) |
| 49 | DMSO-d₆ | 1.47-2.03 (4H, m, -OCH₂C$\underline{H}$₂C$\underline{H}$₂CH₂N-), 2.17 (3H, s, -COCH₃), 2.50-2.83 (6H, m, -N(C$\underline{H}$₃)₂), 2.83-3.33 (2H, m, -C$\underline{H}$₂N-), 3.67 (3H, s, -OCH₃), 3.70-4.10 (2H, m, -OC$\underline{H}$₂-), 6.50-7.40 (7H, m, C₂-H and Ar-H), 7.70-8.10 (1H, m, C₄-H), 10.53-11.37 (1H, br, $\underline{H}$Cl) |
| 50 | DMSO-d₆ | 0.67-2.40 (12H, m, -OCH₂CH₂CH₂N$\underset{|}{\frown}$(CH₂)₅$\frown$), 2.20 (3H, s, -COCH₃), 2.50-2.80 (3H, m, -NCH₃), 2.87-3.50 (3H, m, -C$\underline{H}$₂N-C$\underline{H}$$\frown$), 3.70 (3H, s, -OCH₃), 4.00 (2H, t, J = 6.0, -OC$\underline{H}$₂-), 6.53-7.40 (7H, m, C₂-H and Ar-H), 7.70-8.13 (1H, m, C₄-H), 10.67-11.33 (1H, br, $\underline{H}$Cl) |

| No. | δ (ppm) J = HZ |
|---|---|
| | X NMR |
| 51 DMSO-d₆ | 0.67-2.37 (14H, m, —OCH₂CH₂CH₂CH₂N—(CH₂)₅), 2.20 (3H, s, —COCH₃), 2.4-2.77 (3H, m, —NCH₃), 2.77-3.43 (3H, m, —CH₂N—CH), 3.68 (3H, s, —OCH₃), 3.92 (2H, br t, J = 6.0, —OCH₂—), 6.53-7.40 (7H, m, C₂—H and Ar—H), 7.73-8.10 (1H, m, C₄—H), 10.50-11.07 (1H, br, HCl) |
| 52 DMSO-d₆ | 0.72-2.30 (12H, m, —OCH₂CH₂CH₂N—(CH₂)₅), 2.33 (3H, s, —COCH₃), 2.73 (3H, d, J = 5.0, —NCH₃), 2.92-3.62 (3H, m, —CH₂N—CH), 4.23 (2H, t, J = 5.0, —OCH₂—), 6.75-7.28 (5H, m, C₂—H and Ar—H), 7.30-7.72 (1H, m, C₄—H), 7.33 (1H, dd, J = 9.0, 2.5, C₆'—H), 7.78 (1H, d, J = 2.5, C₂'—H), 11.17-11.85 (1H, br, HCl) |
| 53 DMSO-d₆ | 1.80-2.30 (2H, m, —OCH₂CH₂CH₂N—), 2.24 (3H, s, —COCH₃), 2.60-2.87 (6H, m, —N(CH₃)₂), 2.97-3.43 (2H, m, —CH₂N—), 3.64 (6H, s, —OCH₃ × 2), 3.85 (2H, t, J = 6.0, —OCH₂—), 6.53 (2H, s, C₂'—H and C₆'—H), 6.98 (1H, s, C₂—H), 6.93-7.33 (3H, m, C₅—H, C₆—H and C₇—H), 7.80-8.00 (1H, m, C₄—H), 10.90-11.40 (1H, br, HCl) |
| 54 DMSO-d₆ | 0.90-2.40 (12H, m, —OCH₂CH₂CH₂N—(CH₂)₅), 2.24 (3H, s, —COCH₃), 2.53-2.77 (3H, m, —NCH₃), 2.90-3.40 (3H, m, —CH₂N—CH), 3.68 (6H, s, —OCH₃ × 2), 3.91 (2H, t, J = 6.0, —OCH₂—), 6.58 (2H, s, C₂'—H and C₆'—H), 7.01 (1H, s, C₂—H), 7.00-7.40 (3H, m, C₅—H, C₆—H and C₇—H), 7.77-8.10 (1H, m, C₄—H), 10.68-11.20 (1H, br, HCl) |
| 55 DMSO-d₆ | 0.80-2.30 (14H, m, —OCH₂CH₂CH₂CH₂N—(CH₂)₅), 2.24 (3H, s, —COCH₃), 2.50-2.84 (3H, m, —NCH₃), 2.80-3.40 (3H, m, —CH₂N—CH), 3.63 (6H, s, —OCH₃ × 2), 3.70-4.10 (2H, m, —OCH₂—), 6.55 (2H, s, C₂'—H and C₆'—H), 7.00-7.50 (4H, m, C₂—H, C₅—H, C₆—H and C₇—H), 7.80-8.10 (1H, m, C₄—H), 10.70-11.20 (1H, br, HCl) |
| 56 DMSO-d₆ | 1.90-2.50 (2H, m, —OCH₂CH₂CH₂N—), 2.18 (3H, s, —COCH₃), 2.83 (3H, s, —N—CH₃), 3.10-4.00 (10H, m, |

-continued

| No. | | δ (ppm) J = HZ X NMR |
|---|---|---|
| 57 | DMSO-d$_6$ | —CH$_2$N(CH$_2$)$_2$(CH$_2$)$_2$N—), 4.21 (2H, t, J = 6.0, —OCH$_2$—), 6.60–7.30 (8H, m, C$_2$—H and Ar—H), 7.70–8.10 (1H, m, C$_4$—H), 11.20–12.50 (2H, br, HCl × 2) |
| 58 | DMSO-d$_6$ | 2.22 (3H, s, —COCH$_3$), 2.65–3.55 (14H, m, —CH$_2$N(CH$_2$)$_2$(CH$_2$)$_2$NCH$_2$CH$_2$—), 3.72 (3H, s, —OCH$_3$(A)), 3.75 (3H, s, —OCH$_3$(A)), 6.15 (4H, s, H⟩⟨H × 2), 6.57–7.50 (11H, m, C$_2$—H and Ar—H), 7.70–8.33 (1H, m, C$_4$—H), 11.77–13.03 (4H, br, —CO$_2$H × 4) |
| 59 | DMSO-d$_6$ | 1.75–2.42 (2H, m, —OCH$_2$CH$_2$CH$_2$N—), 2.20 (3H, s, —COCH$_3$), 2.62–3.45 (14H, m, —CH$_2$N(CH$_2$—)(CH$_2$—)N—CH$_2$—), 3.73 (3H, s, —OCH$_3$(A)), 3.77 (3H, s, —OCH$_3$(A)), 4.17 (2H, br t, J = 5.0, —OCH$_2$—), 6.13 (4H, s, H⟩⟨H × 2), 6.60–7.48 (11H, m, C$_2$—H and Ar—H), 7.70–8.18 (1H, m, C$_4$—H), 10.97–12.28 (4H, br, —CO$_2$H × 4) |
|  |  | 2.18 (3H, s, —COCH$_3$), 2.35–2.70 (4H, m, —N(CH$_2$—)(CH$_2$—)), 2.83 (2H, br t, J = 5.0, —CH$_2$N—), 3.27–3.68 (6H, m, —CH$_2$NCOCH$_2$—(CH$_2$—)(CH$_2$—)), 3.70 (6H, s, —OCH$_3$ × 2(A)), 4.20 (2H, br t, J = 5.0, —OCH$_2$—), 6.42–7.47 (1H, m, C$_2$—H and Ar—H), 6.62 (2H, s, H⟩⟨H), 7.67–8.18 (1H, m, C$_4$—H), 11.62 (2H, br s, —CO$_2$H × 2) |
| 60 | | 1.65–2.87 (8H, m, —CH$_2$CH$_2$N(CH$_2$—)(CH$_2$—)NCOCH$_2$—), 2.18 (3H, s, —COCH$_3$), 3.15–3.68 (6H, m, —OCH$_3$ × 2(A)), 4.11 (2H, t, J = 5.5, —OCH$_2$—), 6.60 (2H, s, H⟩⟨H), 6.68–7.48 (11H, m, C$_2$—H and Ar—H), 7.67–8.20 (1H, m, C$_4$—H), 10.87 (2H, br s, —CO$_2$H × 2) |

-continued

| No. | X NMR δ (ppm) J = HZ |
|---|---|
| 61 DMSO-d₆ | 1.83–2.40 (2H, m, —OCH₂CH₂CH₂N—), 2.20 (3H, s, —COCH₃), 2.70–3.63 (10H, m, —CH₂N(CH₂)₂\\(CH₂)₂NCO—), 3.78 (3H, s, —OCH₃(A)), 3.82 (3H, s, —OCH₃(A)), 4.20 (2H, t, J = 6.0, —OCH₂—), 6.62–7.70 (13H, m, C₂—H and Ar—H, —CO\\H/=\\H/H), 7.73–8.20 (1H, m, C₄—H), 11.60–12.30 (1H, br, HCl) |
| 62 DMSO-d₆ | 1.57–2.42 (2H, m, —OCH₂CH₂CH₂N—), 2.23 (3H, s, —COCH₃), 2.60–3.43 (14H, m, —CH₂N(CH₂)₂\\(CH₂)₂NCH₂CH₂—), 3.57 (3H, s, —OCH₃(P)), 3.70 (3H, s, —OCH₃(A)), 3.73 (3H, s, —OCH₃(A)), 4.10 (2H, br t, J = 5.0, —OCH₂—), 6.13 (4H, s, H\\/=\\/H × 2), 6.47 (1H, d, J = 2.0, C₆'—H), 6.60–7.38 (9H, m, C₂—H and Ar—H), 7.68–8.20 (1H, m, C₄—H), 11.37–12.83 (4H, br, —CO₂H × 4) |
| 63 DMSO-d₆ | 1.40–2.00 (4H, m, —OCH₂CH₂CH₂CH₂N—), 2.20 (3H, s, —COCH₃), 2.50–3.20 (14H, m, —CH₂N(CH₂)₂\\(CH₂)₂NCH₂CH₂—), 3.55 (3H, s, —OCH₃(P)), 3.67 (3H, s, —OCH₃(A)), 3.70 (3H, s, —OCH₃(A)), 3.87–4.32 (2H, m, —OCH₂—), 6.45 (1H, d, J = 2.0, C₆'—H), 6.57 (4H, s, H\\/=\\/H × 2), 6.67–7.35 (9H, m, C₂—H and Ar—H), 7.63–8.13 (1H, m, C₄—H), 10.83 (4H, br s, —CO₂H × 4) |
| 64 DMSO-d₆ | 1.40–2.10 (6H, m, —OCH₂(CH₂)₃CH₂N—), 2.22 (3H, s, —COCH₃), 2.60–3.40 (14H, m, —CH₂N(CH₂)₂\\(CH₂)₂NCH₂CH₂—), 3.59 (3H, s, —OCH₃(P)), 3.70 (3H, s, —OCH₃(A)), 3.74 (3H, s, —OCH₃(A)), 3.80–4.30 (2H, m, —OCH₂—), 6.14 (4H, s, H\\/=\\/H × 2), 6.44 (1H, d, J = 2.0, C₆'—H), 6.60–7.30 (9H, m, C₂—H and Ar—H), 7.70–8.20 (1H, m, C₄—H), 10.90–12.20 (4H, br, —CO₂H × 4) |
| 65 DMSO-d₆ | 1.17–2.03 (8H, m, —OCH₂(CH₂)₄CH₂N—), 2.23 (3H, s, —COCH₃), 2.60–3.53 (14H, m, —CH₂N(CH₂)₂\\(CH₂)₂NCH₂CH₂—), 3.57 (3H, s, —OCH₃(P)), 3.70 (3H, s, —OCH₃(A)), 3.73 (3H, s, —OCH₃(A)), 3.87–4.33 (2H, m, —OCH₂—), 6.13 (4H, s, H\\/=\\/H), 6.45 (1H, d, J = 2.0, C₆'—H), 6.60–7.40 (9H, m, C₂—H and Ar—H), 7.67–8.17 (1H, |

-continued

| No. | X NMR δ (ppm) J = HZ |
|---|---|
| 66 DMSO-d6 | 1.40-2.00 (4H, m, —OCH₂CH₂CH₂CH₂N—), 2.20 (3H, s, —COCH₃), 2.60-3.33 (12H, m, —CH₂N$\begin{pmatrix}(CH_2)_2\\(CH_2)_2\end{pmatrix}$NCH₁—), 3.53 (3H, s, —OCH₃(P)), 3.65 (2H, t, J = 5.5, —CH₂OH), 3.87-4.23 (2H, m, —OCH₂—), 6.12 (4H, s, $\underset{H}{\overset{H}{\diagup\!\!\!\diagdown}} \times 2$), 6.43 (1H, d, J = 2.0, C₆'—H), 6.67-7.33 (6H, m, C₂'—H and Ar—H), 7.70-8.10 (1H, m, C₄—H), 9.20-11.20 (5H, br, —CO₂H × 4 and —OH), 11.17-12.67 (4H, br, —CO₂H × 4) |
| 67 DMSO-d6 | 1.50-2.20 (4H, m, —OCH₂CH₂CH₂CH₂N—), 2.25 (3H, s, —COCH₃), 2.70-3.80 (14H, m, —CH₂N$\begin{pmatrix}(CH_2)_2\\(CH_2)_2\end{pmatrix}$NCH₂CH₂—), 3.59 (3H, s, —OCH₃(P)), 3.64 (3H, s, —OCH₃(A)), 3.78 (6H, s, —OCH₃ × 2(A)), 3.84-4.30 (2H, m, —OCH₂—), 6.43 (1H, d, J = 2.0, C₆'—H), 6.63 (2H, s, ), 6.80-7.40 (6H, m, C₂'—H and Ar—H), 7.80-8.10 (1H, m, C₄—H), 11.00-13.50 (2H, br, HCl × 2) |
| 68 DMSO-d6 | 1.60-2.10 (4H, m, —OCH₂CH₂CH₂CH₂N—), 2.21 (3H, s, —COCH₃), 2.60-3.30 (10H, m, —CH₂N$\begin{pmatrix}(CH_2)_2\\(CH_2)_2\end{pmatrix}$N—), 3.56 (3H, s, —OCH₃(P)), 3.74 (3H, s, —OCH₃(A)), 3.77 (3H, s, —OCH₃(A)), 3.79 (3H, s, —OCH₃(A)), 3.60-3.80 (2H, m, —NCH₂—), 3.80-4.20 (2H, m, —OCH₂—), 6.01 (4H, s, $\underset{H}{\overset{H}{\diagup\!\!\!\diagdown}} \times 2$), 6.41 (1H, d, J = 2.0, C₆'—H), 6.72 (1H, d, J = 9.0, 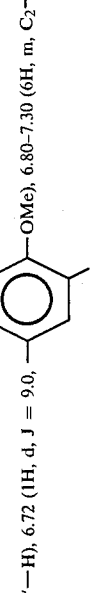), 6.80-7.30 (6H, m, C₂'—H and Ar—H), 7.06 (1H, d, J = 9.0, C₆'—H) |

-continued

| No. | | X NMR δ (ppm) J = HZ |
|---|---|---|
| 69 | DMSO-d$_6$ | ![MeO, OMe, OMe benzene ring with H], 7.60-8.10 (1H, m, C$_4$—H), 10.50-12.50 (4H, br, —CO$_2$H × 4) |
| 70 | DMSO-d$_6$ | 1.50-2.10 (4H, m, —OCH$_2$CH$_2$CH$_2$CH$_2$N—), 2.18 (3H, s, —COCH$_3$), 2.10-3.10 (10H, m, —CH$_2$N[(CH$_2$)$_2$]$_2$N—), 3.57 (3H, s, —OCH$_3$(P)), 3.80-4.20 (2H, m, —OCH$_2$—), 4.37 (1H, s, —NCH—), 6.47 (1H, d, J = 2.0, C$_6$'—H), 6.58 (4H, s, $\underline{H}$ × 2), 6.80-7.70 (15H, m, C$_2$—H and Ar—H), 7.70-8.20 (1H, m, C$_4$—H), 10.61 (4H, br s, —CO$_2$H × 4) |
| 71 | DMSO-d$_6$ | 1.57-2.10 (4H, m, —OCH$_2$CH$_2$CH$_2$CH$_2$N—), 2.23 (3H, s, —COCH$_3$), 2.67-3.43 (12H, m, —CH$_2$N[(CH$_2$)$_2$]$_2$N—), 3.59 (3H, s, —OCH$_3$(P)), 3.74 (3H, s, —OCH$_3$(A)), 3.82 (6H, s, —OCH$_3$ × 2(A)), 3.93-4.23 (2H, m, —CH$_2$OCO—), 4.27-4.67 (2H, m, —OCH$_2$—), 6.10 (4H, s, $\underline{H}$ × 2), 6.45 (1H, d, J = 2.0, C$_6$'—H), 6.67-7.37 (6H, m, C$_2$—H and Ar—H), 7.67-8.13 (1H, m, C$_4$—H), 9.50-11.50 (4H, br, —CO$_2$H × 4) |
| 72 | DMSO-d$_6$ | 1.63-2.78 (8H, m, —CH$_2$CH$_2$N[CH$_2$—,CH$_2$—]NCOCH$_3$), 3.55 (3H, s, —OCH$_3$(P)), 3.70 (6H, s, —OCH$_3$ × 2(A)), 4.03 (2H, t, J = 5.0, —OCH$_2$—), 6.45 (1H, d, J = 2.0, C$_6$'—H), 6.58 (2H, s, $\underline{H}$ × 2), 6.67-7.40 (9H, m, C$_2$—H and Ar—H), 7.63-8.17 (1H, m, C$_4$—H), 10.60 (2H, br s, —CO$_2$H × 2) |
| | | 1.87-2.38 (2H, m, —OCH$_2$CH$_2$CH$_2$N—), 2.20 (3H, s, —COCH$_3$), 2.83-3.47 (6H, m, —CH$_2$N[CH$_2$—,CH$_2$—]), 3.65-4.37 |

| No. | | δ (ppm) J = HZ |
|---|---|---|
| | | -continued X NMR |
| 73 | DMSO-$d_6$ | (6H, m, -OCH$_2$- and -CH$_2$\NCO-/-CH$_2$), 3.53 (3H, s, -OCH$_3$(P)), 3.75 (3H, s, -OCH$_3$(A)), 3.78 (3H, s, -OCH$_3$(A)), 6.03 (2H, s, $\overset{H}{\underset{H}{>}}$), 6.43 (1H, d, J = 2.0, C$_6$'-H), 6.63-7.67 (11H, m, C$_2$-H, -CO-CH(H)(H) and Ar-H), 7.70-8.10 (1H, m, C$_4$-H), 9.83-12.00 (2H, br, -CO$_2$H × 2) |
| 74 | DMSO-$d_6$ | 0.70-1.83 (15H, m, -NCH$_2$(CH$_2$)$_6$CH$_3$), 1.83-2.40 (2H, m, -OCH$_2$CH$_2$CH$_2$N-), 2.28 (3H, s, -COCH$_3$), 2.60-3.43 (12H, m, -CH$_2$N$\underset{(CH_2)_2}{\overset{(CH_2)_2}{<}}$NCH$_2$-), 4.15-4.57 (2H, m, -OCH$_2$-), 6.15 (4H, s, $\overset{H}{\underset{H}{>}}$ × 2), 6.87-7.43 (5H, m, C$_2$-H, C$_5$-H, C$_6$-H, C$_7$-H and C$_3$'-H), 7.75 (1H, d, J = 2.5, C$_6$'-H), 7.70-8.37 (1H, m, C$_4$-H), 8.23 (1H, dd, J = 9.0, 2.5, C$_4$'-H), 11.30-12.50 (4H, br, -CO$_2$H × 4) |
| | | 1.68-2.20 (2H, m, -OCH$_2$CH$_2$CH$_2$N-), 2.27 (3H, s, -COCH$_3$), 2.63-3.50 (14H, m, -CH$_2$N$\underset{(CH_2)_2}{\overset{(CH_2)_2}{<}}$NCH$_2$CH$_2$-), 3.70 (3H, s, -OCH$_3$(A)), 3.73 (3H, s, -OCH$_3$(A)), 4.10-4.60 (2H, m, -OCH$_2$-), 6.10 (4H, s, $\overset{H}{\underset{H}{>}}$ × 2), 6.80 (3H, s, $\underset{H}{\overset{OMe}{\overset{|}{\underset{\bigcirc}{}}}}$OMe), 6.97-7.40 (4H, m, C$_2$-H, C$_5$-H, C$_6$-H and C$_7$-H), 7.28 (1H, d, J = 9.0, C$_3$'-H), 7.72 (1H, d, J = 2.5, C$_6$'-H), 7.77-8.10 (1H, m, C$_4$-H), 8.17 (1H, dd, J = 9.0, 2.5, C$_4$'-H), 11.00-12.27 (4H, br, -CO$_2$H × 4) |
| 75 | DMSO-$d_6$ | 0.58-1.75 (13H, m, -COCH$_2$(CH$_2$)$_5$CH$_3$), 1.75-2.38 (4H, m, -OCH$_2$CH$_2$CH$_2$N- and -NCOCH$_2$-), 2.22 (3H, s, -COCH$_3$), 2.58-3.32 (6H, m, -CH$_2$N$\underset{-CH_2-}{\overset{-CH_2-}{<}}$NCO$\underset{-CH_2}{\overset{-CH_2}{<}}$), 3.32-3.92 (4H, m, -OCH$_2$-), 4.08-4.58 (2H, m, -OCH$_2$-), 6.75-7.48 (5H, m, C$_2$-H, C$_5$-H, C$_6$-H, C$_7$-H and C$_3$'-H), 7.63 (1H, d, J = 2.5, C$_6$-H), 7.65-8.25 (2H, m, C$_4$-H and C$_4$'-H), 10.38 (2H, br s, -CO$_2$H × 2) |

-continued

| No. | δ (ppm) J = HZ X NMR |
|---|---|
| 76 DMSO-$d_6$ | 1.88–2.42 (2H, m, —OCH$_2$CH$_2$CH$_2$N—), 2.29 (3H, s, —COCH$_3$), 2.75–3.65 (10H, m, —CH$_2$N<(CH$_2$)$_2$>(CH$_2$)$_2$>N—), 4.02–4.62 (2H, m, —OCH$_2$—), 4.27 (2H, s, —NCH$_2$CO—), 6.12 (4H, s,  × 2), 6.85–8.38 (12H, m, C$_2$—H and Ar—H), 8.19 (1H, dd, J = 9.0, 2.5, C$_4$'—H), 10.50–11.92 (4H, br, —CO$_2$H × 4) |
| 77 DMSO-$d_6$ | 1.80–2.43 (2H, m, —OCH$_2$CH$_2$CH$_2$N—), 2.28 (3H, s, —COCH$_3$), 2.62–3.58 (12H, m, —CH$_2$N<(CH$_2$)$_2$>(CH$_2$)$_2$>NCH$_2$—), 4.32 (br t, J = 4.0, —OCH$_2$—), 4.96 (1H, J = 6.0, —CH(OH)—), 6.10 (4H, s,  × 2), 6.80–7.42 (5H, m, C$_2$—H, C$_5$—H, C$_6$—H, C$_7$—H and C$_3$'—H), 7.28 (5H, s, —C$_6$H$_5$), 7.62–8.32 (1H, m, C$_4$—H), 7.69 (1H, d, J = 2.5, C$_6$'—H), 8.14 (1H, dd, J = 9.0, 2.5, C$_4$'—H), 9.00–11.75 (5H, br, —CO$_2$H × 4 and —OH) |
| 78 DMSO-$d_6$ | 1.84–2.48 (2H, m, —OCH$_2$CH$_2$CH$_2$N—), 2.35 (3H, s, —COCH$_3$), 2.73–3.67 (10H, m, —CH$_2$N<(CH$_2$)$_2$>(CH$_2$)$_2$>N—), 4.00–4.77 (2H, m, —OCH$_2$—), 4.21 (2H, s, —NCH$_2$CO—), 6.89 (2H, d, J = 8.8,  —OH), 7.03–7.51 (5H, m, C$_2$—H, C$_5$—H, C$_6$—H, C$_7$—H and C$_3$'—H), 7.67–8.51 (3H, m, C$_4$—H, C$_4$'—H and C$_6$'—H), 7.88 (2H, d, J = 8.8, —OH), 10.22 (5H, s, —CO$_2$H × 4 and —OH) |
| 79 DMSO-$d_6$ | 2.12–2.74 (2H, m, —OCH$_2$CH$_2$CH$_2$N—), 2.30 (3H, s, —COCH$_3$), 2.74–3.04 (10H, m, —CH$_2$N<(CH$_2$)$_2$>(CH$_2$)$_2$>N—), 4.17–4.83 |

-continued

| No. | | X NMR δ (ppm) J = HZ |
|---|---|---|
| 80 | CDCl₃ | (2H, m, —OCH₂—), 6.60 (1H, dd, J = 3.8, 1.7, furan-H), 6.87–7.54 (6H, m, C₂—H and Ar—H), 7.69–8.44 (1H, m, C₄'—H), 7.75 (1H, d, J = 2.5, C₆'—H), 7.85 (1H, d, J = 1.7, furan-H), 8.22 (1H, dd, J = 9.0, 2.5, C₄'—H), 11.64–12.51 (1H, br, HCl) |
| 81 | DMSO-d₆ | 2.02–2.72 (2H, m, —OCH₂CH₂CH₂N—), 2.35 (3H, s, —COCH₃), 2.80–3.78 (14H, m, —CH₂N(CH₂)₂(CH₂)₂NCH₂CH₂—), 3.81 (3H, s, —OCH₃(A)), 3.84 (3H, s, —OCH₃(A)), 3.90 (3H, s, —OCH₃(P)), 4.20–4.65 (2H, m, —OCH₂—), 6.73 (3H, s, trimethoxyphenyl-H OMe), 6.93–7.33 (4H, m, C₂—H, C₅—H, C₆—H and C₇—H), 7.37–9.33 (3H, br, C₄—H and HCl × 2), 7.50 (1H, d, J = 2.5, C₄'—H), 7.67 (1H, d, J = 2.5, C₆'—H) |
| 82 | DMSO-d₆ | 1.47–2.00 (4H, m, —OCH₂CH₂CH₂CH₂N—), 2.20 (3H, s, —COCH₃), 2.60–3.30 (14H, m, —CH₂N(CH₂)₂(CH₂)₂NCH₂CH₂—), 3.70 (6H, s, —OCH₃ × 2 (P, A)), 3.73 (3H, s, —OCH₃(A)), 3.73–4.07 (2H, m, —OCH₂—), 6.13 (4H, s, =CH× 2), 6.57–7.33 (10H, m, C₂—H and Ar—H), 7.73–8.07 (1H, m, C₄—H), 11.00–12.17 (4H, br, —CO₂H × 4) |
|  |  | 1.52–2.30 (2H, m, —OCH₂CH₂CH₂N—), 2.17 (3H, s, —COCH₃), 2.35–3.20 (14H, m, —CH₂N(CH₂)₂(CH₂)₂NCH₂CH₂—), 3.67 (3H, s, —OCH₃(A)), 3.69 (3H, s, —OCH₃(A)), 3.92 (2H, t, J = 6.0, —OCH₂—), 6.54 (4H, s, =CH× 2), 6.63–7.32 (11H, m, C₂—H and Ar—H), 7.69–8.10 (1H, m, C₄—H), 11.42 (4H, s, —CO₂H × 4) |

-continued

| No. | X NMR δ (ppm) J = HZ |
|---|---|
| 83 DMSO-d6 | 1.63-2.13 (2H, m, —OCH2CH2CH2N—), 2.19 (3H, s, —COCH3), 2.60-3.30 (14H, m, —CH2N⟨(CH2)2⟩⟨(CH2)2⟩NCH2CH2—), 3.67 (6H, s, —OCH3 × 2 (P, A)), 3.70 (3H, s, —OCH3(A)), 3.93 (2H, t, J = 6.0, —OCH2—), 6.10 (4H, s, H⟨⟩H × 2), 6.47-7.30 (10H, m, C2—H and Ar—H), 7.70-8.10 (1H, m, C4—H), 10.13-12.13 (4H, br, —CO2H × 4) |
| 84 DMSO-d6 | 1.40-2.00 (4H, m, —OCH2CH2CH2CH2N—), 2.20 (3H, s, —COCH3), 2.60-3.33 (14H, m, —CH2N⟨(CH2)2⟩⟨(CH2)2⟩NCH2CH2—), 3.70 (6H, s, —OCH3 × 2 (P, A)), 3.73 (3H, s, —OCH3(A)), 3.97 (2H, t, J = 6.0, —OCH2—), 6.12 (4H, s, H⟨⟩H × 2), 6.53-7.40 (10H, m, C2—H and Ar—H), 7.73-8.17 (1H, m, C4—H), 10.33-12.00 (4H, br, —CO2H × 4) |
| 85 DMSO-d6 | 1.40-2.10 (4H, m, —OCH2CH2CH2CH2N—), 2.24 (3H, s, —COCH3), 2.60-3.40 (14H, m, —CH2N⟨(CH2)2⟩⟨(CH2)2⟩NCH2CH2—), 3.63 (6H, s, —OCH3 × 2 (P)), 3.70 (3H, s, —OCH3(A)), 3.70-4.10 (2H, m, —OCH2—), 3.73 (3H, s, —OCH3(A)), 6.13 (4H, s, H⟨⟩H × 2), 6.54 (2H, s, C2'—H and C6'—H), 6.70-7.40 (7H, m, C2—H and Ar—H), 7.70-8.10 (1H, m C4—H), 10.50-12.00 (4H, br, —CO2H × 4) |
| 86 CDCl3 | 1.51 (9H, s, —C(CH3)3), 2.21 (3H, s, —COCH3), 2.80-3.70 (2H, m, —CH(OH)CH2N—), 3.90-4.40 (2H, m, —OCH2CH—), 4.40-5.10 (1H, br, —H(OH)—), 5.50-5.90 (1H, br, —OH), 6.60-7.30 (8H, m, C2—H and Ar—H), 7.50-8.50 (1H, m, C4—H), 8.00-10.00 (2H, br, —NH— and HCl) |
| 87a DMSO-d6 | 0.90-2.30 (10H, m, —N⟨(CH2)5⟩), 2.20 (3H, s, —COCH3), 2.70-3.00 (3H, m, —NCH3), 3.10-3.70 (3H, m, —CH2N—CH⟨⟩), 4.00-4.30 (2H, m, —OCH2—), 4.30-4.87 (1H, m, —CH(OH)—), 5.50-6.10 (1H, br, —OH), 6.70-7.50 (8H, m, C2—H and Ar—H), 7.80-8.20 (1H, m, C4—H), 9.90-11.00 (1H, br, HCl) |
| 87b DMSO-d6 | 0.90-2.30 (10H, m, —N⟨(CH2)5⟩), 2.20 (3H, s, —COCH3), 2.70-3.00 (3H, m, —NCH3), 3.00-3.80 (3H, m, |

| No. | | δ (ppm) J = HZ |
|---|---|---|
| 88 | CDCl₃ | —C$\underline{H_2}$N—C$\underline{H}$⟨⟩), 3.70–5.60 (2H, br, —C$\underline{H}$(OH)—), 4.00–4.30 (2H, m, —OC$\underline{H_2}$—), 6.80–7.50 (8H, m, C₂—H and Ar—H), 7.70–8.27 (1H, m, C₄—H), 9.70–10.80 (1H, br, $\underline{H}$Cl) |
| 89 | DMSO-d₆ | 1.43 (6H, t, J = 7.0, —N(CH₂C$\underline{H_3}$)₂), 2.32 (3H, s, —COC$\underline{H_3}$), 3.10–3.70 (6H, m, —C$\underline{H_2}$N(CH₂CH₃)₂), 3.9–4.7 2H, m, —OC$\underline{H_2}$CH—), 4.50–5.00 (1H, br, —C$\underline{H}$(OH)—), 5.50–6.10 (1H, br, —O$\underline{H}$), 6.60–7.40 (8H, m, C₂—H and Ar—H), 7.50–8.30 (1H, m, C₄—H), 10.50–11.40 (1H, br, $\underline{H}$Cl) <br><br> 1.50–2.10 (4H, m, —N⟨(C$\underline{H_2}$)₂⟩), 2.00–2.60 (2H, m, —OCH₂C$\underline{H_2}$CH₂N—), 2.20 (3H, s, —COC$\underline{H_3}$), 2.70–3.70 (6H, m, —C$\underline{H_2}$N⟨CH₂/CH₂⟩), 4.17 (2H, t, J = 5.5, —OC$\underline{H_2}$—), 6.70–7.40 (8H, m, C₂—H and Ar—H), 7.80–8.20 (1H, m, C₄—H), 10.90–11.50 (1H, br, $\underline{H}$Cl) |
| 90 | DMSO-d₆ | 1.70–2.30 (2H, m, —OCH₂C$\underline{H_2}$CH₂N—), 2.17 (3H, s, —COC$\underline{H_3}$), 2.30–2.80 (6H, m, —C$\underline{H_2}$N⟨CH₂/CH₂⟩O), 4.11 (2H, t, J = 6.0, —OC$\underline{H_2}$—), 6.70–7.40 (8H, m, C₂—H and Ar—H), 7.70–8.20 (1H, m, C₄—H) |
| 91 | DMSO-d₆ | 1.07–2.07 (7H, m, —OCH₂C$\underline{H_2}$CH₂N⟨CH₂/CH₂⟩C$\underline{H}$⟨CH₂/CH₂⟩), 2.20 (3H, s, —COC$\underline{H_3}$), 2.33–3.50 (8H, m, —C$\underline{H_2}$N), 4.13 (2H, t, J = 6.0, —OC$\underline{H_2}$—), 6.57 (2H, s, ⟩C=C$\underline{H}$), 6.73–7.57 (13H, m, C₂—H and Ar—H), 7.73–8.20 (1H, m, C₄—H), 10.37 (2H, br s, —CO₂$\underline{H}$ × 2) |
| 92 | DMSO-d₆ | 1.32–2.03 (9H, m, —OCH₂C$\underline{H_2}$CH₂N⟨CH₂/CH₂⟩C$\underline{H}$⟨C$\underline{H_2}$/C$\underline{H_2}$⟩), 2.19 (3H, s, —COC$\underline{H_3}$), 2.33–3.36 (8H, m, —C$\underline{H_2}$N⟨C$\underline{H_2}$/C$\underline{H_2}$⟩), |

-continued

| No. | X | NMR δ (ppm) J = HZ |
|---|---|---|
| 93 | CDCl₃ | 3.50 (3H, s, —OCH₃(P)), 3.70-4.20 (2H, m, —OCH₂—), 6.42 (1H, d, J = 2.0, C₆'—H), 6.53 (2H, s, ![structure]), 6.80-7.50 (11H, m, C₂—H and Ar—H), 7.80-8.20 (1H, m, C₄—H), 9.20-9.83 (2H, br, —CO₂H) |
| 94 | DMSO-d₆ | 1.13-2.50 (8H, m, —OCH₂CH₂CH₂N![piperidine structure]), 2.21 (3H, s, —COCH₃), 2.63-3.83 (7H, m, —CH₂N![structure]H), 3.58 (3H, s, —OCH₃(P)), 3.85-4.50 (2H, m, —OCH₂—), 6.43 (1H, d, J = 2.0, C₆'—H), 6.67-8.12 (12H, m, C₂—H and Ar—H), 8.13 (2H, br s, —CO₂H × 2) |
| 95 | DMSO-d₆ | 1.39-2.77 (6H, m, —OCH₂CH₂CH₂N![structure]), 2.29 (3H, s, —COCH₃), 2.78-3.66 (6H, m, —CH₂N![structure]), 3.66-4.06 (1H, m, —CH—OH), 4.10-4.69 (2H, m, —OCH₂—), 6.86-7.60 (5H, m, C₂—H, C₅—H, C₆—H, C₇—H and C₃'—H), 7.71 (1H, d, J = 2.5, C₆'—H), 7.83-8.49 (1H, m, C₄—H), 8.13 (1H, dd, J = 9.0, 2.5, C₄'—H), 8.18 (3H, s, —CO₂H × 2 and —OH) |
| 96 | CDCl₃ | 1.45-2.03 (4H, m, —N![structure]CHCH₂—), 2.27 (3H, s, —COCH₃), 2.05-3.78 (11H, m, —CH₂N![structure]CHCH₂—), 4.11-4.61 (2H, m, —OCH₂—), 6.89-7.55 (10H, m, C₂—H and Ar—H), 7.70 (1H, d, J = 2.5, C₆'—H), 7.81-8.31 (1H, m, C₄—H), 8.28 (1H, dd, J = 9.0, 2.5, C₄'—H), 9.48 (2H, br s, —CO₂H × 2) |
| 97 | CDCl₃ | 1.88-2.85 (4H, m, —OCH₂CH₂CH₂CO₂H), 2.20 (3H, s, —COCH₃), 4.10 (2H, t, J = 5.5, —OCH₂—), 6.60-7.50 (8H, m, C₂—H and Ar—H), 7.70-8.50 (1H, m, C₄—H), 10.88 (1H, br s, —CO₂H) |
| 98 | CDCl₃ | 1.27 (3H, t, J = 7.0, —CO₂CH₂CH₃), 1.88-2.80 (4H, m, —OCH₂CH₂CH₂CO₂—), 2.20 (3H, s, —COCH₃), 4.12 (2H, t, J = 6.0, —OCH₂—), 4.18 (2H, q, J = 7.0, —CO₂CH₂CH₃), 6.60-7.40 (8H, m, C₂—H and Ar—H), 7.80-8.50 (1H, m, C₄—H) |
| 99 | DMSO-d₆ | 1.72-2.80 (8H, m, —OCH₂CH₂CH₂CON![piperazine structure]N—), 2.20 (3H, s, —COCH₃), 2.22 (3H, s, —COCH₃), 2.73 (2H, t, J = 7.0, —NHCH₂CH₂—), 3.48 (2H, q, J = 7.0, —NHCH₂CH₂—), 3.77 (3H, s, —OCH₃(A)), 3.82 (3H, s, —OCH₃(A)), 4.08 (2H, t, J = 5.5, —OCH₂—), 5.70-6.20 (1H, br, —NH—), 6.50-7.50 (11H, m, C₂—H and Ar—H), 7.60-8.50 (1H, m, C₄—H) |

-continued
X NMR
| No. | δ (ppm) J = HZ |
|---|---|
| | J = 4.5, —CON(CH₂—)(CH₂—), 4.12 (2H, t, J = 6.0, —OCH₂—), 6.58 (2H, s, ), 6.72–7.45 (8H, m, C₂—H and Ar—H), 7.80–8.20 (1H, m, C₄—H), 10.70 (2H, br s, —CO₂H × 2) |
| 100 CDCl₃ | 1.90–2.80 (4H, m, —OCH₂CH₂CH₂CON<), 2.20 (3H, s, —COCH₃), 3.65 (8H, br s, —N(CH₂)₂(CH₂)₂O), 4.15 (2H, t, J = 5.5, —OCH₂—), 6.60–7.40 (8H, m, C₂—H and Ar—H), 7.70–8.50 (1H, m, C₄—H) |

Pharmacological Activities

Calcium antagonists have not only potentially beneficial effects in the treatment of many diseases but also serve as valuable research tools to elucidate excitation-contraction coupling in various muscle types (A. Fleckenstein, Ann. Rev. Pharmacol., 17, 149-166, 1977). Therefore, we examined the calcium-antagonistic activity of the compounds of this invention.

Pharmacological test I

The action potentials on the smooth muscles of uterus, teania coli and portal vein are dependent on calcium ion, and therefor these smooth muscle preparations are useful for screening of calcium antagonists. We measured the calcium-antagonistic activity of the compounds by the method using guinea-pig teania coli preparation.

Isolated guinea-pig teania coil was suspended in a 20 ml organ bath with Krebs solution at 32° C. and bubbled with 5% carbon dioxide in oxygen. After equilibration, the muscle was washed with $Ca^{++}$-free Krebs solution, and when the muscle had relaxed to basal level, it was suspended in $Ca^{++}$-free-high-K Krebs solution.

The muscle was exposed to test compounds for 5 minutes before addition of $CaCl_2$, and the contraction evoked by $CaCl_2(3 \times 10^{-4}M)$ was recorded isotonically. The calcium-antagonistic activity was represented by the concentration of test compound which elicited 50% inhibition of $Ca^{++}$-evoked contraction ($IC_{50}$).

As shown in Table XI, the compounds of this invention had calcium-antagonistic activity.

Blood platelet plays an important role only in hemostasis but also in thrombosis. Platelet hyperaggregability leads to an inclease in the number of circulating platelet aggregates, which may contribute toward the development of cardiac arrythmias, cardiac arrest or myocardial infarction. These cardiovascular diseases can be prevented by inhibition of platelet aggregation. Therefor, we screened the influence of test compounds on platelet aggragation in vitro, and found that they have anti-aggregatory activity.

Pharmacological test II

Blood was obtained from an anesthetized rabbit using 0.1 volumes of 3.8% sodium citrate as anticoagulant. Platelet rich plasma(PRP) was isolated by centrifugation at 650 rpm for 10 minutes at room temperature. After preincubation of PRP (0.25 ml) with various concentrations of test compounds (14 μl) for 1 minute at 37° C., collagen (3 μg/ml:final concentration) or ADP (3 μM:final concentration) was added to induce aggregation and the aggregation profiles were monitored with RIKADENKI six-channel aggregometer. The control experiment contained saline instead of test compound.

The anti-aggregatory activity was represented by the concentration of test compound which elicited 50% inhibition of control response.

As shown in the Table XII, the compounds of this invention had anti-aggregatory activity.

TABLE XI

| Calcium-antagonistic activity | |
|---|---|
| Compound No. | $IC_{50}$ [M] |
| 23 | $6.6 \times 10^{-7}$ |
| 33 | $5.2 \times 10^{-7}$ |
| 63 | $6.4 \times 10^{-7}$ |
| 67 | $4.7 \times 10^{-7}$ |

TABLE XII

| Anti-aggregatory activity | |
|---|---|
| Compound No. | $IC_{50}$ [M] |
| 8 | $4.6 \times 10^{-6}$ |
| 21 | $1.3 \times 10^{-6}$ |
| 22 | $1.1 \times 10^{-6}$ |
| 29 | $3.2 \times 10^{-6}$ |
| 54 | $3.1 \times 10^{-6}$ |
| 55 | $2.0 \times 10^{-6}$ |
| 95 | $2.7 \times 10^{-6}$ |

Toxicity test

Acute toxicity of the compounds of this invention is shown in Table XIII.

(animal)

Male ddy-SLC strain rats (4 weeks of age, weighing 19-21 g) were placed in a breeding room of constant temperature and huminity (23±1° C., 55±5%) and fed freely pellet diet and water ad. libitum for a week. Rats showing normal growth were selected for the test.

(method of administration)

Test compounds are suspended in 0.5% tragacanth suspention and administered orally in a dose of 0.5 ml/20 g body weight.

TABLE XIII

| Compound No. | $LD_{50}$ (mg/kg) |
|---|---|
| 29 | >2,000 |
| 63 | ≧3,000 |
| 67 | >1,000 |

The compounds can be administered either orally or parenterally. The dosage forms are tablet, capsule, granule, powder, suppository, injection, etc. The dose is adjusted depending on symptom, dosage form, etc., but usual daily dosage is 1 to 5,000 mg, preferably 10 to 1,000 mg, in one or a few divided doses.

Examples of formulation are shown below.

| Example of formulation | |
|---|---|
| (a) tablet | |
| compound 8 | 30 mg |
| lactose | 150 mg |
| crystalline cellulose | 50 mg |
| calcium carboxymethylcellulose | 7 mg |
| magnesium stearate | 3 mg |
| total | 240 mg |
| compound 21 | 50 mg |
| lactose | 120 mg |
| crystalline cellulose | 60 mg |
| calcium carboxymethylcellulose | 7 mg |
| magnesium stearate | 3 mg |
| total | 240 mg |
| compound 22 | 60 mg |
| lactose | 120 mg |
| crystalline cellulose | 60 mg |
| calcium carboxymethylcellulose | 7 mg |
| magnesium stearate | 3 mg |
| total | 250 mg |
| compound 23 | 40 mg |
| lactose | 150 mg |
| crystalline cellulose | 50 mg |

-continued

| Example of formulation | |
|---|---|
| calcium carboxymethylcellulose | 7 mg |
| magnesium stearate | 3 mg |
| total | 250 mg |
| compound 33 | 70 mg |
| lactose | 110 mg |
| crystalline cellulose | 60 mg |
| calcium carboxymethylcellulose | 7 mg |
| magnesium stearate | 3 mg |
| total | 250 mg |

The tablets may be treated with the common film-coating and further with sugar-coating.

| (b) granule | |
|---|---|
| compound 63 | 30 mg |
| polyvinylpyrrolidone | 25 mg |
| lactose | 385 mg |
| hydroxypropylcellulose | 50 mg |
| talc | 10 mg |
| total | 500 mg |
| compound 29 | 50 mg |
| polyvinylpyrrolidone | 25 mg |
| lactose | 365 mg |
| hydroxypropylcellulose | 50 mg |
| talc | 10 mg |
| total | 500 mg |
| (c) powder | |
| compound 54 | 30 mg |
| lactose | 500 mg |
| starch | 440 mg |
| colloidal silica | 30 mg |
| total | 1000 mg |
| compound 67 | 50 mg |
| lactose | 480 mg |
| starch | 440 mg |
| colloidal silica | 30 mg |
| total | 1000 mg |
| (d) capsule | |
| compound 55 | 30 mg |
| lactose | 102 mg |
| crystalline cellulose | 56 mg |
| colloidal silica | 2 mg |
| total | 190 mg |
| compound 95 | 50 mg |
| glycerol | 329.8 mg |
| butyl p-hydroxybenzoate | 0.02 mg |
| total | 380 mg |

UTILITY IN AN INDUSTRIAL FIELD

This invention offers novel compounds which are useful for therapeutic agent.

What we claim is:

1. A compound of the formula (I) and salts thereof,

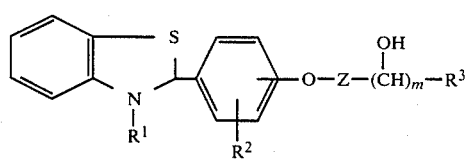

(I)

wherein
$R^1$ is lower alkanoyl;
$R^2$ is at least one group selected from the group consisting of hydrogen, lower-alkyl, lower-alkoxy, hydroxy, halogen, nitro, halogeno-lower-alkyl and sulfamoyl;
$R^3$ is

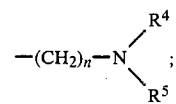

$R^4$ and $R^5$, may be same or different and are selected from the group consisting of hydrogen, lower alkyl, cyclohexyl, phenyl-lower alkyl and substituted phenyl-lower alkyl wherein the phenyl nucleus is substituted by at least one group selected from the group consisting of lower alkyl, hydroxy, chloro, bromo, loweralkoxy, nitro, cyano, acetamino and lower alkylamino, hydroxy-lower alkyl, 3-pyridyl-lower alkyl, 1-piperidyl-lower alkyl and phenylcarbonyl-lower alkyl;
Z is straight or branched alkylene having 1 to 6 carbon atoms;
m is 0 or 1;
n is 0 or 1;
wherein the terms lower alkyl, lower alkoxy and lower alkanoyl refer to groups having 1 to 6 carbon atoms.

2. A compound as in claim 1 wherein m is 0.

3. A compound as in claim 1 wherein m is 1, n is 1 and Z is —CH$_2$—.

4. A compound as in claim 1 wherein $R^1$ is acetyl.

5. A compound as in claim 1 wherein $R^2$ is hydrogen.

6. A compound as in claim 2 wherein $R^2$ is methoxy or nitro.

7. A compound as in claim 2 wherein $R^4$ is methyl and $R^5$ is cyclohexyl.

8. A compound as in claim 2 wherein $R^4$ is methyl and $R^5$ is 2-(3,4-dimethoxyphenyl)ethyl.

9. A compound as in claim 2 wherein $R^4$ is hydrogen and $R^5$ is 3-pyridylmethyl.

10. 3-Acetyl-2-[2-(3-t-butylamino-2-hydroxypropoxy)phenyl]benzothiazoline as in claim 1.

11. 3-Acetyl-2-[2-[3-(N-cyclohexyl-N-methylamino)propoxy]phenyl]benzothiazoline as in claim 1.

12. 3-Acetyl-2-[2-[5-(N-cyclohexyl-N-methylamino)pentoxy]-5-methoxyphenyl]benzothiazoline as in claim 1.

13. 3-Acetyl-2-[2-[6-(N-cyclohexyl-N-methylamino)hexyloxy]-5-methoxyphenyl]benzothiazoline as in claim 1.

14. 3-Acetyl-2-[4-[3-(N-cyclohexyl-N-methylamino)propoxy]-3,5-dimethoxyphenyl]benzothiazoline as in claim 1.

15. 3-Acetyl-2-[4-[3-(N-cyclohexyl-N-methylamino)butoxy]-3,5-dimethoxyphenyl]benzothiazoline as in claim 1.

16. 3-Acetyl-2-[2-[3-(N-cyclohexyl-N-methylamino)propoxy]-5-nitrophenyl]benzothiazoline as in claim 1.

17. 3-Acetyl-2-[2-[4-[N-[2-(3,4-dimethoxyphenyl)ethyl]-N-methylamino]butoxy]-3-methoxyphenyl]benzothiazoline as in claim 1.

18. 3-Acetyl-2-[5-nitro-2-[3-[(3-pyridylmethyl)amino]propoxy]phenyl]benzothiazoline as in claim 1.

19. A pharmaceutical composition comprising (i) a compound as in claim 1 in an amount sufficient for treatment for cardiovascular diseases and at least one pharmaceutically acceptable excipient.

20. A method of treatment for cardiovascular diseases which comprises administering a composition comprising a compound as in claim 1 and at least one pharmaceutically acceptable excipient.

21. A compound of the formula (I) and salts thereof,

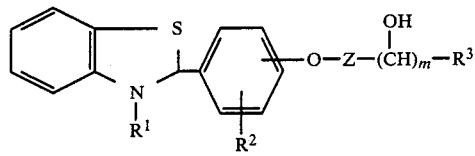 (I)

wherein
- $R^1$ is lower alkanoyl;
- $R^2$ is at least one group selected from the group consisting of hydrogen, lower-alkoxy, chloro, nitro and hydroxy;
- $R^3$ is

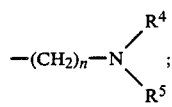

$R^4$ and $R^5$ which may be same or different and are selected from the group consisting of hydrogen, lower alkyl, cyclohexyl, hydroxy-lower alkyl, phenyl-lower alkyl and substituted phenyl-lower alkyl wherein the phenyl nucleus is substituted by at least one lower alkoxy group, diphenyl-lower alkyl or 3-pyridyl-lower alkyl;

Z is straight or branched alkylene having 1 to 6 carbon atoms;

m is 0;

n is 0 or 1, wherein the terms lower alkyl, lower alkoxy and lower alkanoyl refer to groups having 1 to 6 carbon atoms.

22. A method of treatment for cardiovascular diseases which comprises administering a composition comprising a compound as in claim 21 and at least one pharmaceutically acceptable excipient.

23. A compound of the formula (I) and salts thereof,

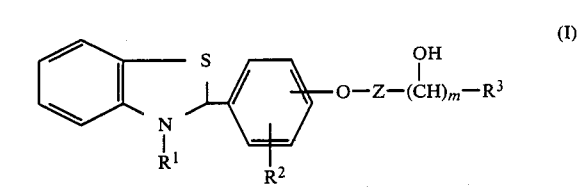 (I)

wherein
- $R^1$ is acetyl;
- $R^2$ is one or more hydrogen, or one or two group(s) selected from methoxy, chloro, nitro and hydroxy;
- $R^3$ is

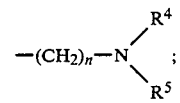

$R^4$ and $R^5$ may be same or different and are selected from the group consisting of hydrogen, lower alkyl, cyclohexyl, hydroxyethyl, benzyl and phenyl-lower alkyl wherein the phenyl nucleus is substituted by one to three methoxy group(s), 1,2-diphenylethyl or 3-pyridylmethyl;

Z is straight or branched alkylene having 1 to 6 carbon atoms;

m is 0;

n is 0, wherein the term lower alkyl refers to a group having 1 to 6 carbon atoms.

24. A method of treatment for cardiovascular diseases which comprises administering a composition comprising a compound as in claim 23 and at least one pharmaceutically acceptable excipient.

* * * * *

UNITED STATES PATENT AND TRADEMARK OFFICE
CERTIFICATE OF CORRECTION

PATENT NO. : 4,552,969

DATED : November 12, 1985

INVENTOR(S) : IWAO et al

It is certified that error appears in the above-identified patent and that said Letters Patent is hereby corrected as shown below:

Column 2, line 26, change "microbiral" to --microbial--.

Column 4, formula (b), change " $+(CH_2)_q$ " to -- $-(CH_2)_q$ --.

Column 5, line 21, change "descrived" to --described--.

Column 5, line 62, change "Ethy acetate" to
    --Ethyl acetate-- .

Column 6, line 48, change "wiht" to --with--.

Column 7, line 32, change "bnezothiazoline" to
    --benzothiazoline--.

Column 8, line 61, change "oder" to --order--.

UNITED STATES PATENT AND TRADEMARK OFFICE
CERTIFICATE OF CORRECTION

PATENT NO. : 4,552,969

DATED : November 12, 1985

INVENTOR(S) : IWAO et al

It is certified that error appears in the above-identified patent and that said Letters Patent is hereby corrected as shown below:

Columns 19/20, TABLE IV, line corresponding to

"Compound No. 59*³" under the designation

"IR(KBr,cm⁻¹)", first row of numbers, change

"3430" to --3420--.

Column 20, TABLE IV, line corresponding to

"Compound No. 60*³", under the designation

"IR(KBr,cm⁻¹)", last row of numbers, change

"11155" to --1155--.

Column 22, TABLE IV, the line corresponding to

"Compound No. 77*²", under the heading designation

"IR(KBr,cm⁻¹)", first row of numbers, change "392"

to --3392--.

Columns 25/26, TABLE VIII, the first formula under the column headed "R⁹", change "  " to --  --.

UNITED STATES PATENT AND TRADEMARK OFFICE
CERTIFICATE OF CORRECTION

PATENT NO. : 4,552,969

DATED : November 12, 1985

INVENTOR(S) : IWAO et al

Page 3 of 4

It is certified that error appears in the above-identified patent and that said Letters Patent is hereby corrected as shown below:

Columns 25/26, TABLE VIII, the line corresponding to "Compound No.90", the formula under the column headed "$R^9$", change "-H⟨ ⟩O" to --  -N⟨ ⟩O --.

Column 25/26, TABLE VIII, the line corresponding to "Compound No. 91*$^2$", second row of numbers, change "1239" to --1238--.

Column 64, the line corresponding to "86 CDCl$_3$", middle of line 2, change " -H(OH)-) " to --(1H, br, -CH(OH)-)--.

Column 71, line 36, change "inclease" to --increase--.

Column 71, line 42, change "aggragation" to --aggregation--.

Column 72, line 31, change "suspention" to --suspension--.

UNITED STATES PATENT AND TRADEMARK OFFICE
CERTIFICATE OF CORRECTION

PATENT NO. : 4,552,969

DATED : November 12, 1985

INVENTOR(S) : IWAO et al

It is certified that error appears in the above-identified patent and that said Letters Patent is hereby corrected as shown below:

Column 73 (Claim 1), last line, change "lower-alkyl,
  lower-alkoxy" to --lower-n-alkyl, lower-n-alkoxy--.

Column 75 (Claim 21), line 17, change "lower-alkoxy" to
  --lower-n-alkoxy--.

Signed and Sealed this

Twenty-fourth Day of May, 1994

Attest:

BRUCE LEHMAN

*Attesting Officer*   *Commissioner of Patents and Trademarks*